US010821217B2

(12) United States Patent
Pate

(10) Patent No.: US 10,821,217 B2
(45) Date of Patent: Nov. 3, 2020

(54) FISTULA FORMATION DEVICES AND METHODS THEREFOR

(71) Applicant: TVA Medical, Inc., Austin, TX (US)

(72) Inventor: Thomas Diffley Pate, Austin, TX (US)

(73) Assignee: TVA MEDICAL, INC., Austin, TX (US)

( * ) Notice: Subject to any disclaimer, the term of this patent is extended or adjusted under 35 U.S.C. 154(b) by 1311 days.

(21) Appl. No.: 14/214,503

(22) Filed: Mar. 14, 2014

(65) Prior Publication Data

US 2014/0276335 A1 Sep. 18, 2014

Related U.S. Application Data

(60) Provisional application No. 61/785,509, filed on Mar. 14, 2013.

(51) Int. Cl.
*A61M 1/36* (2006.01)
*A61B 18/14* (2006.01)
(Continued)

(52) U.S. Cl.
CPC ........... *A61M 1/3655* (2013.01); *A61B 17/11* (2013.01); *A61B 18/1477* (2013.01);
(Continued)

(58) Field of Classification Search
CPC . A61M 1/3655; A61M 25/0127; A61B 34/73; A61B 17/11; A61B 18/1477;
(Continued)

(56) References Cited

U.S. PATENT DOCUMENTS 3,649,850 A 3/1972 Davis
3,827,436 A 8/1974 Stumpf et al.
(Continued)

FOREIGN PATENT DOCUMENTS

CA 2883209 A1 4/2014
CN 1730123 A 2/2006
(Continued)

OTHER PUBLICATIONS

Maybury et al. (The Effect of Roll Angle on the Performance of Halbach Arrays, Sep. 16, 2008).*
(Continued)

*Primary Examiner* — Ariana Zimbouski
(74) *Attorney, Agent, or Firm* — Dinsmore & Shohl LLP

(57) ABSTRACT

Described here are devices, systems, and methods for forming a fistula between two blood vessels. Generally, the systems may comprise a first catheter and a second catheter, which may comprise one or more fistula-forming elements. The first and second catheters may comprise one or more magnetic elements, which may be used to assist in bringing the first and catheters in closer proximity to facilitate fistula formation. In some variations, the magnetic elements may have magnetization patterns such that the flux generated by the magnetic elements is locally concentrated. In some instances, the system may comprise a magnetic control device, which may comprise a magnet, and may be used to increase or create an attractive force between the first and second catheters.

18 Claims, 16 Drawing Sheets

(51) Int. Cl.
*A61B 17/11* (2006.01)
*A61B 34/00* (2016.01)
*A61B 17/12* (2006.01)
*A61B 18/00* (2006.01)
*A61M 25/01* (2006.01)
*A61B 17/00* (2006.01)
*A61B 17/22* (2006.01)

(52) U.S. Cl.
CPC .......... *A61B 18/1492* (2013.01); *A61B 34/73* (2016.02); *A61B 17/1204* (2013.01); *A61B 17/12136* (2013.01); *A61B 2017/00876* (2013.01); *A61B 2017/1107* (2013.01); *A61B 2017/1139* (2013.01); *A61B 2017/22071* (2013.01); *A61B 2018/00577* (2013.01); *A61B 2018/00601* (2013.01); *A61B 2018/1425* (2013.01); *A61M 25/0127* (2013.01)

(58) Field of Classification Search
CPC .......... A61B 18/1492; A61B 2034/733; A61B 2034/731; A61B 1/00158
See application file for complete search history.

(56) References Cited

U.S. PATENT DOCUMENTS

| | | |
|---|---|---|
| 4,416,664 A | 11/1983 | Womack |
| 4,802,475 A | 2/1989 | Weshahy |
| 5,313,943 A | 5/1994 | Houser et al. |
| 5,697,909 A | 12/1997 | Eggers et al. |
| 5,800,487 A | 9/1998 | Mikus et al. |
| 5,830,222 A | 11/1998 | Makower |
| 5,830,224 A | 11/1998 | Cohn et al. |
| 5,895,404 A | 4/1999 | Ruiz |
| 5,971,979 A | 10/1999 | Joye et al. |
| 6,004,330 A | 12/1999 | Middleman et al. |
| 6,032,677 A | 3/2000 | Blechman et al. |
| 6,039,730 A | 3/2000 | Rabin et al. |
| 6,068,638 A | 5/2000 | Makower |
| 6,099,542 A | 8/2000 | Cohn et al. |
| 6,159,225 A | 12/2000 | Makower |
| 6,190,353 B1 | 2/2001 | Makower et al. |
| 6,197,025 B1 | 3/2001 | Grossi et al. |
| 6,217,575 B1 | 4/2001 | DeVore et al. |
| 6,231,587 B1 | 5/2001 | Makower |
| 6,256,525 B1 | 7/2001 | Yang et al. |
| 6,283,988 B1 | 9/2001 | Laufer et al. |
| 6,287,306 B1 | 9/2001 | Kroll et al. |
| 6,302,875 B1 | 10/2001 | Makower et al. |
| 6,327,505 B1 | 12/2001 | Medhkour et al. |
| 6,347,247 B1 | 2/2002 | Dev et al. |
| 6,355,029 B1 | 3/2002 | Joye et al. |
| 6,357,447 B1 | 3/2002 | Swanson et al. |
| 6,379,353 B1 | 4/2002 | Nichols |
| 6,383,180 B1 | 5/2002 | LaLonde et al. |
| 6,400,976 B1 | 6/2002 | Champeau |
| 6,428,534 B1 | 8/2002 | Joye et al. |
| 6,461,356 B1 | 10/2002 | Patterson |
| 6,464,665 B1 | 10/2002 | Heuser |
| 6,464,723 B1 | 10/2002 | Callol |
| 6,468,268 B1 | 10/2002 | Abboud et al. |
| 6,475,214 B1 | 11/2002 | Moaddeb |
| 6,475,226 B1 | 11/2002 | Belef et al. |
| 6,527,724 B1 | 3/2003 | Fenici |
| 6,527,769 B2 | 3/2003 | Langberg et al. |
| 6,542,766 B2 | 4/2003 | Hall et al. |
| 6,544,230 B1 | 4/2003 | Flaherty et al. |
| 6,569,158 B1 | 5/2003 | Abboud et al. |
| 6,569,162 B2 | 5/2003 | He |
| 6,579,311 B1 | 6/2003 | Makower |
| 6,585,650 B1 | 7/2003 | Solem |
| 6,592,577 B2 | 7/2003 | Abboud et al. |
| 6,635,053 B1 | 10/2003 | LaLonde et al. |
| 6,655,386 B1 | 12/2003 | Makower et al. |
| 6,656,173 B1 | 12/2003 | Palermo |
| 6,663,625 B1 | 12/2003 | Ormsby et al. |
| 6,669,709 B1 | 12/2003 | Cohn et al. |
| 6,673,085 B1 | 1/2004 | Berg |
| 6,676,657 B2 | 1/2004 | Wood |
| 6,682,525 B2 | 1/2004 | LaLonde et al. |
| 6,695,878 B2 | 2/2004 | McGuckin et al. |
| 6,709,444 B1 | 3/2004 | Makower |
| 6,719,756 B1 | 4/2004 | Muntermann |
| 6,726,697 B2 | 4/2004 | Nicholas et al. |
| 6,733,494 B2 | 5/2004 | Abboud et al. |
| 6,736,808 B1 | 5/2004 | Motamedi et al. |
| 6,761,708 B1 | 7/2004 | Chiu |
| 6,761,714 B2 | 7/2004 | Abboud et al. |
| 6,780,181 B2 | 8/2004 | Kroll et al. |
| 6,849,073 B2 | 2/2005 | Hoey et al. |
| 6,855,143 B2 | 2/2005 | Davison et al. |
| 6,887,234 B2 | 5/2005 | Abboud et al. |
| 6,911,026 B1 | 6/2005 | Hall et al. |
| 6,932,814 B2 | 8/2005 | Wood |
| 6,936,024 B1 | 8/2005 | Houser |
| 6,960,209 B2 | 11/2005 | Clague et al. |
| 6,971,983 B1 | 12/2005 | Cancio |
| 6,981,972 B1 | 1/2006 | Farley et al. |
| 7,041,128 B2 | 5/2006 | McGuckin, Jr. et al. |
| 7,059,330 B1 | 6/2006 | Makower et al. |
| 7,060,063 B2 | 6/2006 | Marion et al. |
| 7,094,235 B2 | 8/2006 | Francischelli |
| 7,155,293 B2 | 12/2006 | Westlund et al. |
| 7,179,270 B2 | 2/2007 | Makower |
| 7,189,231 B2 | 3/2007 | Clague et al. |
| 7,214,234 B2 | 5/2007 | Rapacki et al. |
| 7,231,260 B2 | 6/2007 | Wallace et al. |
| 7,250,051 B2 | 7/2007 | Francischelli |
| 7,288,075 B2 | 10/2007 | Parihar et al. |
| 7,303,554 B2 | 12/2007 | LaLonde et al. |
| 7,306,598 B2 | 12/2007 | Truckai et al. |
| 7,335,198 B2 | 2/2008 | Eggers et al. |
| 7,341,063 B2 | 3/2008 | Garbibaldi et al. |
| 7,367,341 B2 | 5/2008 | Anderson et al. |
| 7,374,567 B2 | 5/2008 | Heuser |
| 7,387,636 B2 * | 6/2008 | Cohn ............... A61B 17/11 606/167 |
| 7,407,506 B2 | 8/2008 | Makower |
| 7,628,768 B2 | 12/2009 | Faul et al. |
| 7,702,387 B2 | 4/2010 | Stevenson et al. |
| 7,727,268 B2 | 6/2010 | Cunniffe et al. |
| 7,744,596 B2 | 6/2010 | Young et al. |
| 7,811,281 B1 | 10/2010 | Rentrop |
| 7,828,814 B2 | 11/2010 | Brenneman et al. |
| 7,846,172 B2 | 12/2010 | Makower |
| 7,849,860 B2 | 12/2010 | Makower et al. |
| 7,857,809 B2 | 12/2010 | Drysen |
| 7,881,797 B2 | 2/2011 | Griffin et al. |
| 7,955,326 B2 | 6/2011 | Paul et al. |
| 7,967,769 B2 | 6/2011 | Faul et al. |
| 7,967,770 B2 | 6/2011 | Li et al. |
| 7,976,536 B2 | 7/2011 | Farley et al. |
| 8,010,208 B2 | 8/2011 | Nimer et al. |
| 8,048,016 B2 | 11/2011 | Faul et al. |
| 8,052,680 B2 | 11/2011 | Hassett et al. |
| 8,062,321 B2 | 11/2011 | Heuser et al. |
| RE43,007 E | 12/2011 | LaLonde et al. |
| 8,075,555 B2 | 12/2011 | Truckai et al. |
| 8,088,171 B2 | 1/2012 | Brenneman |
| 8,100,899 B2 | 1/2012 | Doty et al. |
| 8,118,809 B2 | 2/2012 | Paul et al. |
| 8,135,467 B2 | 3/2012 | Markowitz et al. |
| 8,142,454 B2 | 3/2012 | Harrison et al. |
| 8,192,425 B2 | 6/2012 | Mirza et al. |
| 8,200,466 B2 | 6/2012 | Spilker et al. |
| 8,226,592 B2 | 7/2012 | Brenneman et al. |
| 8,231,618 B2 | 7/2012 | Viswanathan et al. |
| 8,236,014 B2 | 8/2012 | Brenneman et al. |
| 8,262,649 B2 | 9/2012 | Francischelli |
| 8,273,095 B2 | 9/2012 | Brenneman et al. |
| 8,328,797 B2 | 12/2012 | Wilson et al. |
| 8,333,758 B2 | 12/2012 | Joye et al. |
| 8,361,061 B2 | 1/2013 | Esch et al. |

(56) References Cited

U.S. PATENT DOCUMENTS

| | | |
|---|---|---|
| 8,366,707 B2 | 2/2013 | Kassab et al. |
| 8,382,697 B2 | 2/2013 | Brenneman et al. |
| 8,409,196 B2 | 4/2013 | Durgin et al. |
| 8,413,664 B2 | 4/2013 | Appling |
| 8,414,572 B2 | 4/2013 | Davison et al. |
| 8,419,681 B2 | 4/2013 | Sell |
| 8,439,909 B2 | 5/2013 | Wang et al. |
| 8,454,587 B2 | 6/2013 | LaLonde et al. |
| 8,475,441 B2 | 7/2013 | Babkin et al. |
| 8,486,062 B2 | 7/2013 | Belhe et al. |
| 8,486,064 B2 | 7/2013 | Van Wyk et al. |
| 8,551,032 B2 | 10/2013 | Faul et al. |
| 8,574,185 B2 | 11/2013 | Faul et al. |
| 8,585,700 B2 | 11/2013 | Katou |
| 8,608,754 B2 | 12/2013 | Wensel et al. |
| 8,641,724 B2 | 2/2014 | Brenneman et al. |
| 8,649,879 B2 | 2/2014 | DiGiore et al. |
| 8,676,309 B2 | 3/2014 | Deem et al. |
| 8,685,014 B2 | 4/2014 | Babkin et al. |
| 8,700,179 B2 | 4/2014 | Pianca et al. |
| 8,715,281 B2 | 5/2014 | Barlow et al. |
| 8,758,334 B2 | 6/2014 | Coe et al. |
| 8,784,409 B2 | 6/2014 | Robilotto et al. |
| 8,771,267 B2 | 7/2014 | Kunis et al. |
| 8,790,341 B2 | 7/2014 | Pappone et al. |
| 8,876,699 B2 | 11/2014 | Sato et al. |
| 8,876,815 B2 | 11/2014 | Coe et al. |
| 8,882,765 B2 | 11/2014 | Kassab et al. |
| 8,911,435 B2 | 12/2014 | Katoh et al. |
| 8,951,251 B2 | 2/2015 | Willard |
| 9,017,323 B2 | 4/2015 | Miller et al. |
| 9,039,702 B2 | 5/2015 | Miller et al. |
| 9,072,880 B2 | 7/2015 | Phillips et al. |
| 9,089,316 B2 | 7/2015 | Baust et al. |
| 9,108,018 B2 | 8/2015 | Dickinson et al. |
| 9,155,827 B2 | 10/2015 | Franano |
| 9,204,916 B2 | 12/2015 | Lalonde |
| 9,259,340 B2 | 2/2016 | Heuser et al. |
| 9,283,034 B2 | 3/2016 | Katoh et al. |
| 9,307,992 B2 | 4/2016 | Wilson et al. |
| 9,314,329 B2 | 4/2016 | Dickinson et al. |
| 9,326,792 B2 | 5/2016 | Dickinson et al. |
| 9,364,280 B2 | 6/2016 | Zarins et al. |
| 9,402,560 B2 | 8/2016 | Organ et al. |
| 9,414,885 B2 | 8/2016 | Willard |
| 9,439,728 B2 | 9/2016 | Hull et al. |
| 9,445,868 B2 | 9/2016 | Hull et al. |
| 9,452,015 B2 | 9/2016 | Kellerman et al. |
| 9,486,276 B2 | 11/2016 | Rios et al. |
| 9,623,217 B2 | 4/2017 | Pillai |
| 9,706,998 B2 | 7/2017 | Dickinson et al. |
| 9,782,201 B2 | 10/2017 | Dickinson et al. |
| 9,782,533 B2 | 10/2017 | Brenneman et al. |
| 10,045,817 B2 | 8/2018 | Miller et al. |
| 10,265,206 B2 | 4/2019 | Heuser et al. |
| 10,517,637 B2 | 12/2019 | Dickinson et al. |
| 10,543,308 B2 | 1/2020 | Lenihan et al. |
| 10,575,974 B2 | 3/2020 | De Pablo Pena et al. |
| 10,596,356 B2 | 3/2020 | Lenihan et al. |
| 2001/0029384 A1 | 10/2001 | Nicholas et al. |
| 2002/0072739 A1 | 6/2002 | Lee et al. |
| 2002/0113678 A1* | 8/2002 | Creighton ............ H01F 7/0273 335/306 |
| 2002/0151945 A1 | 10/2002 | Gobin et al. |
| 2003/0009163 A1 | 1/2003 | Messing et al. |
| 2003/0220674 A1 | 11/2003 | Anderson et al. |
| 2004/0059211 A1 | 3/2004 | Patel et al. |
| 2004/0059280 A1 | 3/2004 | Makower et al. |
| 2004/0167506 A1 | 8/2004 | Chen |
| 2004/0215220 A1 | 10/2004 | Dolan et al. |
| 2004/0236360 A1 | 11/2004 | Cohn et al. |
| 2005/0033401 A1 | 2/2005 | Cunniffe et al. |
| 2005/0065509 A1 | 3/2005 | Coldwell et al. |
| 2005/0245925 A1 | 11/2005 | Iki et al. |
| 2005/0251120 A1 | 11/2005 | Anderson et al. |
| 2006/0079897 A1* | 4/2006 | Harrison ............ A61B 17/66 63/900 |
| 2006/0111704 A1 | 5/2006 | Brenneman et al. |
| 2007/0173878 A1 | 7/2007 | Heuser |
| 2007/0185567 A1 | 8/2007 | Heuser et al. |
| 2007/0203515 A1 | 8/2007 | Heuser et al. |
| 2007/0203572 A1 | 8/2007 | Heuser et al. |
| 2007/0293856 A1 | 12/2007 | Paul et al. |
| 2008/0021532 A1 | 1/2008 | Kveen et al. |
| 2008/0051626 A1 | 2/2008 | Sato et al. |
| 2008/0065019 A1 | 3/2008 | Heuser et al. |
| 2008/0091192 A1 | 4/2008 | Paul et al. |
| 2008/0119879 A1 | 5/2008 | Brenneman et al. |
| 2008/0140061 A1 | 6/2008 | Toubia et al. |
| 2008/0161901 A1 | 7/2008 | Heuser et al. |
| 2008/0171944 A1 | 7/2008 | Brenneman et al. |
| 2008/0183164 A1 | 7/2008 | Elkins et al. |
| 2008/0188848 A1 | 8/2008 | Deutmeyer et al. |
| 2008/0275442 A1 | 11/2008 | Paul et al. |
| 2008/0312577 A1 | 12/2008 | Drasler et al. |
| 2009/0036872 A1* | 2/2009 | Fitzgerald ........ A61M 25/0127 604/533 |
| 2009/0076324 A1 | 3/2009 | Takayama et al. |
| 2009/0093791 A1 | 4/2009 | Heuser |
| 2009/0112119 A1 | 4/2009 | Kim |
| 2009/0118722 A1 | 5/2009 | Ebbers et al. |
| 2009/0124847 A1 | 5/2009 | Doty et al. |
| 2009/0198232 A1 | 8/2009 | Young et al. |
| 2009/0248148 A1* | 10/2009 | Shaolian ............ A61F 2/2448 623/2.37 |
| 2009/0275876 A1 | 11/2009 | Brenneman et al. |
| 2009/0281379 A1 | 11/2009 | Binmoeller et al. |
| 2009/0318849 A1 | 12/2009 | Hobbs et al. |
| 2010/0004623 A1 | 1/2010 | Hamilton, Jr. et al. |
| 2010/0010488 A1 | 1/2010 | Kassab et al. |
| 2010/0082058 A1 | 4/2010 | Kassab |
| 2010/0130835 A1 | 5/2010 | Brenneman et al. |
| 2010/0198206 A1 | 8/2010 | Levin |
| 2010/0204691 A1 | 8/2010 | Bencini |
| 2010/0222664 A1 | 9/2010 | Lemon et al. |
| 2010/0256616 A1 | 10/2010 | Katoh et al. |
| 2010/0280316 A1 | 11/2010 | Deitz et al. |
| 2010/0280514 A1 | 11/2010 | Zerfas et al. |
| 2010/0286705 A1 | 11/2010 | Vassiliades, Jr. |
| 2010/0292685 A1 | 11/2010 | Katoh et al. |
| 2010/0298645 A1* | 11/2010 | Deutch ............ A61B 17/0218 600/201 |
| 2011/0015657 A1 | 1/2011 | Brenneman et al. |
| 2011/0112427 A1 | 5/2011 | Phillips et al. |
| 2011/0118735 A1 | 5/2011 | Abou-Marie et al. |
| 2011/0201990 A1 | 8/2011 | Franano |
| 2011/0213309 A1 | 9/2011 | Young et al. |
| 2011/0218476 A1* | 9/2011 | Kraemer ............ A61B 17/1114 604/8 |
| 2011/0270149 A1 | 11/2011 | Faul et al. |
| 2011/0288392 A1 | 11/2011 | de la Rama et al. |
| 2011/0288544 A1 | 11/2011 | Verin et al. |
| 2011/0306959 A1 | 12/2011 | Kellerman et al. |
| 2011/0306993 A1 | 12/2011 | Hull et al. |
| 2011/0319976 A1 | 12/2011 | Iyer et al. |
| 2012/0010556 A1 | 1/2012 | Faul et al. |
| 2012/0022518 A1 | 1/2012 | Levinson |
| 2012/0035539 A1 | 2/2012 | Tegg |
| 2012/0046678 A1 | 2/2012 | LeMaitre et al. |
| 2012/0059398 A1 | 3/2012 | Pate et al. |
| 2012/0065652 A1 | 3/2012 | Cully et al. |
| 2012/0078342 A1 | 3/2012 | Vollkron et al. |
| 2012/0089123 A1 | 4/2012 | Organ et al. |
| 2012/0101423 A1 | 4/2012 | Brenneman |
| 2012/0116354 A1 | 5/2012 | Heuser |
| 2012/0157992 A1 | 6/2012 | Smith et al. |
| 2012/0209377 A1 | 8/2012 | Machold et al. |
| 2012/0215088 A1 | 8/2012 | Wang et al. |
| 2012/0239021 A1 | 9/2012 | Doty et al. |
| 2012/0277736 A1 | 11/2012 | Francischelli |
| 2012/0281330 A1 | 11/2012 | Abbott et al. |
| 2012/0289953 A1 | 11/2012 | Berzak et al. |
| 2012/0296262 A1 | 11/2012 | Ogata et al. |

(56) References Cited

U.S. PATENT DOCUMENTS

| | | | |
|---|---|---|---|
| 2012/0302935 A1* | 11/2012 | Miller | A61B 17/32072 604/8 |
| 2013/0041306 A1 | 2/2013 | Faul et al. | |
| 2013/0056876 A1 | 3/2013 | Harvey et al. | |
| 2013/0110105 A1 | 5/2013 | Vankov | |
| 2013/0172881 A1 | 7/2013 | Hill et al. | |
| 2013/0190744 A1 | 7/2013 | Avram et al. | |
| 2013/0190754 A1 | 7/2013 | Paul et al. | |
| 2013/0216351 A1* | 8/2013 | Griffin | F01D 25/06 415/1 |
| 2013/0226170 A1 | 8/2013 | Seddon et al. | |
| 2013/0261368 A1 | 10/2013 | Schwartz | |
| 2013/0282000 A1 | 10/2013 | Parsonage | |
| 2014/0031674 A1 | 1/2014 | Newman et al. | |
| 2014/0094791 A1 | 4/2014 | Hull et al. | |
| 2014/0100557 A1 | 4/2014 | Bohner et al. | |
| 2014/0100562 A1 | 4/2014 | Sutermeister et al. | |
| 2014/0107642 A1 | 4/2014 | Rios et al. | |
| 2014/0166098 A1 | 6/2014 | Kian et al. | |
| 2014/0188028 A1 | 7/2014 | Brenneman et al. | |
| 2014/0276335 A1 | 9/2014 | Pate | |
| 2015/0005759 A1 | 1/2015 | Welches et al. | |
| 2015/0011909 A1 | 1/2015 | Holmin et al. | |
| 2015/0018810 A1 | 1/2015 | Baust et al. | |
| 2015/0057654 A1 | 2/2015 | Leung et al. | |
| 2015/0057687 A1 | 2/2015 | Gittard et al. | |
| 2015/0080886 A1 | 3/2015 | Miller et al. | |
| 2015/0094645 A1 | 4/2015 | Omar-Pasha | |
| 2015/0112195 A1 | 4/2015 | Berger et al. | |
| 2015/0134055 A1 | 5/2015 | Spence et al. | |
| 2015/0141836 A1 | 5/2015 | Naumann et al. | |
| 2015/0164573 A1 | 6/2015 | Delaney | |
| 2015/0196356 A1 | 7/2015 | Kauphusman et al. | |
| 2015/0196360 A1 | 7/2015 | Grantham et al. | |
| 2015/0201962 A1 | 7/2015 | Kellerman et al. | |
| 2015/0258308 A1 | 9/2015 | Pate | |
| 2015/0297259 A1 | 10/2015 | Matsubara et al. | |
| 2015/0313668 A1 | 11/2015 | Miller et al. | |
| 2015/0320472 A1 | 11/2015 | Ghaffari et al. | |
| 2016/0022345 A1 | 1/2016 | Baust et al. | |
| 2016/0058452 A1 | 3/2016 | Brenneman et al. | |
| 2016/0058956 A1 | 3/2016 | Cohn et al. | |
| 2016/0067449 A1 | 3/2016 | Misener et al. | |
| 2016/0082234 A1 | 3/2016 | Schwartz et al. | |
| 2016/0128855 A1 | 5/2016 | Heuser et al. | |
| 2016/0135881 A1 | 5/2016 | Katoh et al. | |
| 2016/0184011 A1 | 6/2016 | Krishnan | |
| 2016/0206317 A1 | 7/2016 | Dickinson et al. | |
| 2017/0119464 A1 | 5/2017 | Rios et al. | |
| 2017/0172679 A1 | 6/2017 | Doty et al. | |
| 2017/0202603 A1 | 7/2017 | Cohn et al. | |
| 2017/0202616 A1 | 7/2017 | Pate et al. | |
| 2018/0000512 A1 | 1/2018 | Dickinson et al. | |
| 2018/0083228 A1 | 3/2018 | Yang et al. | |
| 2018/0116522 A1 | 5/2018 | Brenneman et al. | |
| 2018/0206845 A1 | 7/2018 | Brenneman et al. | |
| 2018/0344396 A1 | 12/2018 | Miller et al. | |
| 2020/0061338 A1 | 2/2020 | Pate | |

FOREIGN PATENT DOCUMENTS

| | | |
|---|---|---|
| CN | 101730557 A | 6/2010 |
| EP | 0889705 A1 | 1/1999 |
| EP | 0923912 A2 | 6/1999 |
| JP | 11-512640 A | 11/1999 |
| JP | 2004-501720 A | 1/2004 |
| JP | 3493464 B2 | 2/2004 |
| RU | 2168951 C1 | 6/2001 |
| WO | 1997/033522 A1 | 9/1997 |
| WO | 9956640 A1 | 11/1999 |
| WO | 2002/002163 A2 | 1/2002 |
| WO | 2008010039 A2 | 1/2008 |
| WO | WO-2009/005644 A2 | 1/2009 |
| WO | WO-2009/005644 A3 | 1/2009 |
| WO | WO-2011/100625 A2 | 8/2011 |
| WO | WO-2011/100625 A3 | 8/2011 |
| WO | 2012/068273 A1 | 5/2012 |
| WO | 2013112584 A1 | 8/2013 |
| WO | WO-2014/052919 A1 | 4/2014 |
| WO | WO-2014/059351 A1 | 4/2014 |
| WO | WO-2014/137830 A1 | 9/2014 |
| WO | WO-2014/153229 A1 | 9/2014 |
| WO | WO-2015/040557 A1 | 3/2015 |
| WO | WO-2015/061614 A1 | 4/2015 |
| WO | WO-2015/085119 A1 | 6/2015 |
| WO | 2015108984 A1 | 7/2015 |
| WO | WO-2015/138998 A1 | 9/2015 |
| WO | 2016033380 A1 | 3/2016 |
| WO | 2017124059 A1 | 7/2017 |
| WO | 2017124060 A1 | 7/2017 |
| WO | 2018057095 A1 | 3/2018 |

OTHER PUBLICATIONS

Choi et al., Design of a Halbach Magnet Array Based on Optimization Techniques, IEEE Transactions on Magnetics, vol. 44, No. 10, Oct. 2008, pp. 2361-2366. (Year: 2008).*

Maybury et al., "The Effect of Roll Angle on the Performance of Halbach Arrays," University of California—San Diego, Center for Magnetic Recording Research (2008), 19 pages. (Year: 2008).*

International Preliminary Report on Patentability received for PCT Patent Application No. PCT/US2011/061026, dated May 30, 2013, 8 pages.

International Search Report and Written Opinion received for PCT Patent Application No. PCT/US2011/061026, dated Feb. 23, 2012, 8 pages.

International Search Report & Written Opinion received for PCT Patent Application No. PCT/US2013/064657, dated Jan. 10, 2014, 9 pages.

Office Action Received for Australian Patent Application No. 2011328926, dated Jun. 2, 2014, 4 pages.

Non Final Office Action received for U.S. Appl. No. 13/298,169, dated Aug. 8, 2014, 15 pages.

International Search Report and Written Opinion received for PCT Patent Application No. PCT/US2014/029731, dated Aug. 22, 2014, 12 pages.

Notice of Allowance received for U.S. Appl. No. 13/298,169, dated Dec. 31, 2014, 10 pages.

Notice of Allowance received for U.S. Appl. No. 13/298,169, dated Mar. 11, 2015, 4 pages.

Final Office Action received for U.S. Appl. No. 14/052,477, dated Mar. 10, 2016, 11 pages.

Non Final Office Action received for U.S. Appl. No. 14/052,477, dated Jul. 29, 2015, 15 pages.

Notice of Allowance received for U.S. Appl. No. 14/550,747, dated Jan. 23, 2015, 3 pages.

Notice of Acceptance received for Australian Patent Application No. 2011328926, dated Jun. 30, 2015, 2 pages.

Notice of Allowance received for Chinese Patent Application No. 201180065285.1, dated Nov. 26, 2015, 4 pages (2 pages of English Translation and 2 pages of Official Copy).

Office Action received for Chinese Patent Application No. 201180065285.1, dated Mar. 20, 2015, 7 pages (2 pages of English Translation and 5 pages of Official Copy).

Office Action received for Singapore Patent Application No. 201303477-2, dated Apr. 21, 2015, 8 pages.

Written Opinion received for Singapore Patent Application No. 201303477-2, dated Jun. 12, 2014, 10 pages.

Office Action received for Japanese Patent Application No. 2013-539007, dated Sep. 8, 2015, 9 pages (5 pages of English Translation and 4 pages of Official Copy).

Notice of Allowance received for Mexican Patent Application No. Mx/a/2013/005393, dated Oct. 30, 2015, 3 pages (2 pages of English Translation and 1 page of Official copy).

Banasik et al., "A Rare Variant Route of the Ulnar Artery does not Contraindicate the Creation of a Fistula in the Wrist of a Diabetic

(56) References Cited

OTHER PUBLICATIONS

Patient with End-Stage Renal Disease", Postepy Hig Med Dosw (online), vol. 65, 2011, pp. 654-657.
Bharat et al., "A Novel Technique of Vascular Anastomosis to Prevent Juxta-Anastomotic Stenosis following Arteriovenous Fistula Creation", Journal of Vascular Surgery, vol. 55, No. 1, Jan. 2012, pp. 274-280.
Bode et al., "Clinical Study Protocol for the Arch Project Computational Modeling for Improvement of Outcome after Vascular Access Creation", J. Vasc. Access, vol. 12, No. 4, 2011, pp. 369-376.
Davidson et al., "Duplex Ultrasound Evaluation for Dialysis Access Selection and Maintenance: A Practical Guide", The Journal of Vascular Access, vol. 9, 2008, pp. 1-9.
Gracz et al., "Proximal Forearm Fistula for Maintenance Hemodialysis", Kidney International, vol. 11, 1977, pp. 71-75.
Jennings et al., "Primary Arteriovenous Fistula Inflow Proximalization for Patients at High Risk for Dialysis Access-Associated Ischemic Steal Syndrome", Journal of Vascular Surgery, 2011, 2 pages.
Kinnaert et al., "Ulnar Arteriovenous Fistula for Maintenance Haemodialysis", The British Journal of Surgery, vol. 58, No. 9, Sep. 1971, pp. 641-643.
Morale et al., "Venae Cornitantes as a Potential Vascular Resource to Create Native Arteriovenous Fistulae", J Vasc Access, vol. 12, No. 3, 2011, pp. 211-214.
International Preliminary Report on Patentability received for PCT Patent Application No. PCT/US2013/064657 dated Apr. 23, 2015, 8 pages.
International Preliminary Report on Patentability received for PCT Patent Application No. PCT/US2014/029731, dated Sep. 24, 2015, 10 pages.
International Search Report and Written Opinion received for PCT Patent Application No. PCT/US2015/020604, dated Jun. 17, 2015, 8 pages.
Shenoy, Surendra, "Surgical Anatomy of Upper Arm: What is needed for AVF Planning", The Journal of Vascular Access, vol. 10, 2009, pp. 223-232.
Vachharajani, Tushar J., "Atlas of Dialysis Vascular Access", Wake Forest University School of Medicine, 2010, 77 pages.
Whittaker et al., "Prevention Better than Cure. Avoiding Steal Syndrome with Proximal Radial or Ulnar Arteriovenous Fistulae", J Vasc Access, vol. 12, No. 4, 2011, pp. 318-320.
Extended European Search Report dated Oct. 19, 2016, for EP Application No. 14 770 396.1, filed on Mar. 14, 2014, 7 pages.
Final Office Action dated Oct. 6, 2016, for U.S. Appl. No. 14/697,451, filed Apr. 27, 2015, 11 pages.
Non-Final Office Action dated May 2, 2016, for U.S. Appl. No. 14/697,451, filed Apr. 27, 2015, 12 pages.
Notice of Allowance dated Jul. 12, 2016, for U.S. Appl. No. 14/052,477, filed Oct. 11, 2013, 7 pages.
U.S. Appl. No. 15/344,332, filed Nov. 4, 2016, by Rios et al.
International Search Report and Written Opinion dated Jun. 1, 2017, for PCT Patent Application No. PCT/US2017/13613, filed Jan. 15, 2017, 18 pages.
International Search Report and Written Opinion dated Jan. 6, 2016, from the International Searching Authority for Application No. PCTUS2015047274 filed Aug. 27, 2015, 12 pages.
Invitation to Pay Additional Fees and, where Applicable, Protest Fee, dated Oct. 22, 2015, issued by the International Searching Authority for Application No. PCTUS2015047274 filed Aug. 27, 2015, 2 pages.
International Search Report and Written Opinion dated May 19, 2017, by the International Searching Authority for Application No. PCT/US2017/013610, filed Jan. 15, 2017, 10 pages.
Final Office Action dated Aug. 29, 2017, for U.S. Appl. No. 14/697,451, filed Apr. 27, 2015, 16 pages.
International Search Report and Written Opinion dated Sep. 28, 2017, by the International Searching Authority for Application No. PCT/US2017/042937, filed Jul. 19, 2017, 11 pages.
Extended European Search Report dated Oct. 16, 2017, for EP Application No. 11841243.6, filed Nov. 16, 2011, 6 pages.
Extended European Search Report for EP Application No. 17739123.2.
Hakim et al., "Ulnar artery-based free forearm flap: Review of Specific anatomic features in 322 cases and related literature," Heand & Neck, Dec. 2013 (published online:2014), Wiley Online Library.
Dura Magnetics, Inc., "Benefits and Drawbacks to Using Halbach Arrays", https://www.duramag.com/techtalk/halbach-arrays/benefits-and-drawbacks-to-using-halbach-arrays/, 2019.
International Search Report and Written Opinion dated Mar. 31, 2017, for PCT Patent Application No. PCT/US2017/13611, filed on Jan. 15, 2017, 10 pages.
Invitation to Pay Additional Fees and, Where Applicable, Protest Fee dated Mar. 31, 2017, for PCT Application No. PCT/US17/13613, filed Jan. 15, 2017, 3 pages.
Non-Final Office Action dated Apr. 13, 2017, for U.S. Appl. No. 14/697,451, filed Apr. 27, 2015, 14 pages.
Extended European Search Report pertaining to EP Patent Application No. 17853586.0, dated Apr. 29, 2020.

* cited by examiner

FISTULA FORMATION DEVICES AND METHODS THEREFOR

CROSS-REFERENCE TO RELATED APPLICATIONS

This application claims priority to U.S. Provisional Application Ser. No. 61/785,509, filed on Mar. 14, 2013, and titled "FISTULA FORMULATION DEVICES AND METHODS THEREFOR," the content of which is hereby incorporated in its entirely.

FIELD

The current invention relates to devices and methods for forming a fistula. The devices and methods may be used to form a fistula between two blood vessels.

BACKGROUND

A fistula is generally a passageway formed between two internal organs. Forming a fistula between two blood vessels can have one or more beneficial functions. For example, the formation of a fistula between an artery and a vein may provide access to the vasculature for hemodialysis patients. Specifically, forming a fistula between an artery and a vein allows blood to flow quickly between the vessels while bypassing the capillaries. In other instances, a fistula may be formed between two veins to form a veno-venous fistula. Such a veno-venous fistula may be used to help treat portal venous hypertension. Generally, fistula formation requires surgical dissection of a target vein, and transecting and moving the vein for surgical anastomosis to the artery. It may therefore be useful to find improved ways to form a fistula between two blood vessels.

BRIEF SUMMARY

Described here are devices and systems for forming a fistula. In some variations, the systems described here may comprise a first catheter and a second catheter. The first catheter may comprise one or more fistula-forming elements. Additionally or alternatively, the second catheter may comprise one or more fistula-forming elements. The first and second catheters may comprise one or more magnetic elements, which may be used to move the first and second catheters in closer proximity to facilitate fistula formation. In some variations, the magnetic elements may have magnetization patterns such that the magnetic field generated by the magnetic elements is locally concentrated. In some instances, the system may comprise a magnetic control device, which may comprise a magnet, and may be used to increase or create an attractive force between the first and second catheters.

In some variations of the systems described here, the system may comprise a first catheter comprising a first magnetic element and a second catheter comprising a second magnetic element, such that at least one of the first and second catheters comprises a fistula-forming element. The fistula-forming element may be any suitable structure, such as an electrode. In some variations, the first magnetic element may be configured to produce a magnetic field that is stronger on a first side of the first magnetic element than on a second side of the magnetic element. In some variations, the first magnetic element may comprise a plurality of regions each having a polarity. The plurality of regions of the first magnetic element may be configured such that the polarity of each region is rotated a first angle relative to the polarity of an immediately-preceding region in a proximal-to-distal direction. In some of these variations, the second magnetic element may comprise a plurality of regions each having a polarity. The plurality of regions of the second magnetic element may be configured such that the polarity of each region is rotated a second angle relative to the polarity of an immediately-preceding region in a proximal-to-distal direction. The first angle may or may not be the same as the second angle. The first and second angles may be any suitable angles (e.g., about 30 degrees, about 45 degrees, about 90 degrees). In some variations, the first magnetic element may have a plurality of regions such that the polarity of each region is rotated a first angle clockwise relative to an immediately-preceding region, and the second magnetic element may have a plurality of regions such that each region is rotated a first angle counterclockwise relative to an immediately-preceding region.

In some variations, the systems may comprise a magnetic control device, which may comprise a housing having a contact surface for placement against the skin, a magnet, and a control element connected to the magnet and moveable relative to the housing such that the control element may move the magnet relative to contact surface. In some variations, the magnet may comprise a magnetic array having a magnetization pattern. In some variations, the housing and/or control element may comprise one or more finger rings.

DETAILED DESCRIPTION OF THE INVENTION

Figure 1:
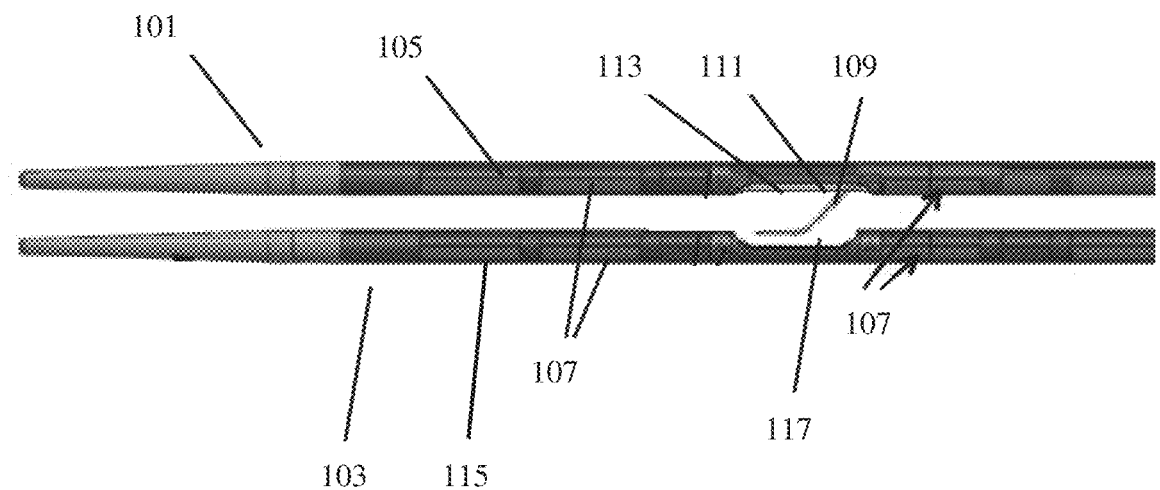
FIG. 1 is an illustrative depiction of a variation of a system described here comprising a first catheter and a second catheter.

Generally described here are systems, devices, and methods for forming a fistula between blood vessels. The fistula may be, for example, an arteriovenous fistula between an artery and a vein, or a veno-venous fistula between two veins. Generally, to form a fistula between two blood vessels, one or more catheters may be advanced in a minimally invasive fashion through the vasculature to a target fistula formation site. Typically, a catheter may be placed in each of the two blood vessels, such that a first catheter may be positioned in a first blood vessel and a second catheter may be positioned in a second blood vessel. Accordingly, the systems described here may comprise a first catheter and a second catheter.

The first and second catheters may have one or more magnetic elements, which may be configured to aid in positioning and/or alignment of the catheters. For example, in some instances the first catheter may comprise one or more magnetic elements which may be attracted to one or more magnetic elements of the second catheter, which may act to pull the first and second catheters toward each other. In some variations, the magnetic elements may have magnetization patterns such that the strength of a magnetic field generated by the magnetic element is greater on one side of the magnet than on an opposite side.

In some variations, the systems may also comprise a magnetic control device for applying a magnetic force to the first and second catheters using an external magnet positioned outside of the body. The magnetic control device may comprise a control element that may help to adjust the position of the external magnet in a controlled manner. In some instances, the external magnet may have a magnetization pattern such that the strength of the magnetic field generated by the external magnet is greater on one side of the magnet than on an opposite side. It should be appreciated that each catheter may or may not have the same configuration of elements, and that some catheters may be different from and/or complementary to other catheters.

Devices

Catheters

As mentioned above, the systems described here typically comprise a first catheter and a second catheter. Any suitable catheter or catheters may be used with the systems described here to form the fistulas using the methods described here. For example, in some variations the system may comprise one or more of the catheters described in U.S. patent application Ser. No. 13/298,169, filed on Nov. 16, 2011 and titled "DEVICES AND METHODS FOR FORMING A FISTULA," the contents of which are hereby incorporated by reference in their entirety. Generally, each catheter may have a proximal end, a distal end, and an intermediate portion connecting the proximal and distal ends. The proximal end may comprise one or more adaptors or handles, which may be utilized to help aid in advancement, positioning, and/or control of the catheter within the vasculature, and may further be used to actuate one or more components of the catheter and/or introduce one or more fluids or substances into and/or through the catheter. The catheter may comprise one or more elements that may aid in fistula formation. For example, one or more portions (e.g., the distal end and/or the intermediate portion) of the catheter may comprise one or more elements, such as magnets, that may help to align the catheter with another catheter positioned in a related blood vessel, and/or help to bring the catheters into closer approximation, as will be described in more detail below. As the catheters are brought in to closer approximation, the blood vessels within which the catheters are positioned may be brought into closer approximation, which may aid in fistula formation. Additionally or alternatively, one or more portions (e.g., the distal end and/or an intermediate portion) of the catheter may comprise one or more mechanisms for forming a fistula.

The catheters may additionally comprise one or more lumens or passageways extending at least partially along or through the catheter, and may be used to pass one or more guidewires, one or more drugs or fluids (e.g., contrast agents, perfusion fluids), combinations thereof, or the like at least partially along or through the catheter, but need not comprise these lumens or passageways. The distal tip of the catheter may be configured to aid in advancement of the catheter and/or to be atraumatic. In some variations, the tip may comprise one or more rapid exchange portions or other lumens for advancement of the catheter over a guidewire. In still other variations, the tip portion may have a guidewire attached to or otherwise integrally formed with the catheter.

Additionally, in some variations the catheters may further comprise one or more external expandable elements (e.g., a balloon, expandable cage, mesh, or the like) that may help position a catheter within a blood vessel, but need not comprise one or more external expandable elements. Additionally or alternatively, the one or more expandable elements may affect the flow of blood through one or more blood vessels (e.g., by temporarily occluding blood flow through the blood vessel, dilating one or more portions of a blood vessel, constricting one or more portions of a blood vessel, or the like). In some instances, one or more expandable elements may act to temporarily anchor a portion of the catheter relative to a blood vessel. In variations where the catheter comprises one or more shape-changing elements, as will be described in more detail below, the use of an expandable element to temporarily anchor a portion of the catheter relative to a blood vessel may aid in altering the shape of the catheter. It should be appreciated that the catheters described here may have any combination of the aforementioned elements.

FIG. 1 shows an illustrative variation of a catheter system that may be used to form a fistula between two vessels. As shown there, the system may comprise a first catheter (101) and a second catheter (103). The first catheter (101) may comprise a catheter body (105), one or more magnetic elements (107), and a fistula-forming element (109) which may be activated to form a fistula. In some variations, the fistula-forming element (109) may be advanced to project out of an opening (111) in the catheter body (105). In some variations, the first catheter (101) may comprise a housing (113), which may help protect other components of the first catheter (101) during fistula formation. For example, when the fistula-forming element (109) comprises an electrode configured to ablate tissue, the housing (113) may comprise one or more insulating materials which may shield or otherwise protect one or more components of the first catheter (101) from heat that may be generated by the electrode during use.

As shown in FIG. 1, the second catheter (103) may also comprise a catheter body (115) and one or more magnetic elements (107). In variations where the first catheter (101) comprises a fistula-forming element (109) configured to project out the catheter body (105) of the first catheter (101), such as the variation depicted in FIG. 1, the catheter body (115) of the second catheter (103) may comprise a recess (117) therein, which may be configured to receive the fistula-forming element (109) as it passes through tissue. In some of these variations, the recess (117) may be coated by an insulating material (not shown), which may be configured to protect one or more components of the second catheter (103) from being damaged by the fistula-forming element (109) (e.g., the insulating material may shield one or more components of the second catheter (103) from heat that may be generated by the fistula-forming element (109)). While shown in FIG. 1 as having a recess (117), it should also be appreciated that in some variations the second catheter (103) may not comprise a recess (117). In some variations, the second catheter may comprise a fistula-forming element (not shown) in addition to or instead of the fistula-forming element (109) of the first catheter (109), as will be described in detail below.

Fistula-Forming Elements

As mentioned above, the catheters described here may comprise one or more elements for forming a fistula. The fistula-forming element may comprise any element capable of forming a fistula between two vessels, such as those elements described in U.S. patent application Ser. No.

13/298,169, which was previously incorporated by reference in its entirety. For example, the fistula-forming element may comprise one or more electrical mechanisms (e.g., electrodes or electrocautery mechanisms); one or more mechanical mechanisms (e.g., blades, lances, needles, or the like); one or more chemical devices (e.g., enzyme-releasing devices); one or more cryogenic-cautery devices; one or more laser ablation devices; and/or combinations thereof, and the like. A catheter may have any suitable number (e.g., zero, one, two, three, or four or more) and combination of these fistula-forming elements. The fistula-forming elements may be located in or on any suitable portion of the catheter (e.g., the distal end, an intermediate portion, or combinations thereof). In variations where a catheter comprises two or more fistula-forming elements, multiple fistula-forming elements may be used to create multiple fistulas, either simultaneously or sequentially. In other variations, multiple fistula-forming elements may interact to form a single fistula.

In variations where a system comprising multiple catheters is used to create a fistula between two blood vessels, each catheter may comprise a fistula-forming element, but need not. Indeed, in some of these variations, only one catheter may comprise a fistula-forming element. In some of these instances, the other catheter may still help align the catheters and/or approximate the blood vessels, but may not directly contribute to tissue removal. In variations where multiple catheters each comprise a fistula-forming element, the catheters may have complimentary fistula-forming elements. For example, in variations where two or more catheters comprise electrodes, one catheter may comprise an electrode that acts as an active electrode, while another catheter may comprise an electrode that acts as a passive or ground electrode.

In some variations of the catheters described here, a catheter may comprise one or more electrodes for use in forming a fistula. When a fistula-forming element comprises an electrode, it may be used to ablate or otherwise remove the tissue in contact with the electrode in order to form the fistula. If a fistula-forming element comprises an electrode, the electrode may be configured as described in U.S. patent application Ser. No. 13/298,169, which was previously incorporated by reference in its entirety.

In the embodiment shown in FIG. 1, the fistula-forming element (109) of the first catheter (101) may comprise an electrode. The electrode may be selectively moved from a position in which the electrode is retained or otherwise held in the catheter body (105) to a position in which the electrode extends away from the catheter body (105) (e.g., through the opening (111)), and the electrode may also be selectively moved back to a retracted/low-profile position (either the same or a different position as the previous retracted position) following ablation of tissue. This may allow the electrode to be maintained in a low-profile configuration during positioning of the catheter. In some variations, the electrode may be biased toward an extended position when not otherwise restrained by the catheter body (105).

Magnetic Elements

As mentioned above, the first and second catheters of the systems described here may comprise one or more magnetic elements. Generally, the magnetic elements may be configured to be attracted to one or more magnetic fields (e.g., produced by one or more magnetic elements of another catheter, produced by one or more magnets positioned external to the body). The magnetic element or elements may help to align or otherwise reposition the catheters when placed in the vasculature. In some instances, a system may comprise first and second catheters each having one or more magnetic elements, such that magnetic elements of the first catheter may be attracted to magnetic elements of the second catheter to bring the catheters in closer approximation. Additionally or alternatively, one or more external magnetic elements may be positioned outside of the body, and may attract the one or more magnetic elements of the first and/or second catheters to help reposition the first and/or second catheters, as will be described in more detail below. In other instances, one or more magnetic elements may help to ensure that one or more catheters are in proper axial or rotational alignment relative to another catheter or catheters, such as described in further detail in U.S. patent application Ser. No. 13/298,169, which was previously incorporated by reference in its entirety, which may facilitate alignment of one or more fistula-forming elements relative to a target fistula-formation site.

When the catheters described here comprise a magnetic element, it should be appreciated that the magnetic element may be configured to generate a magnetic field, but need not. For example, in some variations a catheter may have a magnetic element formed from one or more ferromagnetic materials configured to become temporarily magnetized when exposed to a magnetic field. In these variations, when the magnetic element is placed in a magnetic field (such as one produced by a magnetic element of another catheter), the temporary magnetization may provide an attractive force to the catheter to move or reposition the catheter. Examples of suitable ferromagnetic materials which may be temporarily, but are not limited to, cobalt, gadolinium, iron, nickel, alloys of these metals with or without other metals such as alnico, chemical compounds such as ferrites, and/or a combination of any of these metals or their alloys.

In instances where the magnetic element is configured to generate a magnetic field, the magnetic element may comprise a permanent magnet or an electromagnet. When a magnetic element comprises a permanent magnet, the magnet may be made of any suitable material capable of generating a magnetic field. In some instances, the magnetic elements may be permanent magnets made out of ferromagnetic materials. For example, in some variations, the magnetic elements may comprise one or more rare-earth magnets (e.g. samarium-cobalt magnets or neodymium magnets), and/or cobalt, gadolinium, iron, nickel, alloys of these metals with or without other metals such as alnico, chemical compounds such as ferrites, and/or a combination of any of these metals or their alloys. When a magnetic element comprises an electromagnet, the electromagnet may be selectively activated to produce a magnetic field. For example, when one or more catheters of the systems described here comprise one or more electromagnets, the electromagnets may be activated before fistula formation to bring the blood vessels within which the catheters are located in closer approximation; they may remain activated during fistula formation to hold the vessels in closer approximation during the fistula-formation procedure; and then they may be deactivated after the fistula-formation procedure is complete. When a catheter comprises multiple electromagnet-based magnetic elements, these magnetic elements may be independently activated or may be activated as a group.

When the systems described here comprise a first catheter and a second catheter each comprising one or more magnetic elements, each catheter may comprise any combination of permanent magnets, ferromagnetic elements, or electromagnets. For example, in some variations, the first catheter may include only permanent magnets. In these variations, the second catheter may include only permanent magnets, only ferromagnetic elements, only electromagnets, or a mix of some or all of these elements. In other variations the first catheter may include only ferromagnetic elements. Again, the second catheter may include only permanent magnets, only ferromagnetic elements, only electromagnets, or a mix of some or all of these elements. In still other variations, the first catheter may include a permanent magnets and ferromagnetic elements. In these variations, the second catheter may include only permanent magnets, ferromagnetic elements, only electromagnets, or a mix of some or all of these elements.

When the catheters of the systems described here comprise one or more magnetic elements, each catheter may comprise any number of individual magnetic elements (e.g., one, two, three, four, five, six, seven, or eight or more, etc.). In variations where a catheter comprises a plurality of magnetic elements, these magnetic elements may be grouped into one or more arrays. The magnetic elements or arrays may be located inside or outside of a catheter body or both. The magnetic elements or arrays may be positioned anywhere along the length of the catheter. In some variations where the system comprises a first catheter having a fistula-forming element (such as the first catheter (101) shown in FIG. 1), the first catheter may comprise one or more magnetic elements or arrays proximal to a fistula-forming element. Additionally or alternatively, the first catheter may comprise one or more magnetic elements or arrays distal to a fistula-forming element. In some variations in which a system comprises a second catheter comprising a fistula-forming element, the second catheter may comprise one or more magnetic elements or arrays proximal to the fistula-forming element. Additionally or alternatively, when the second catheter comprises a fistula-forming element, the second catheter may comprise one or more magnetic elements or arrays distal to the fistula-forming element. In variations where both the first and second catheters comprise one or more magnetic elements or arrays, each magnetic element or array in the first catheter may be configured to align with one or more magnetic elements or arrays in a second catheter. Each magnetic element may be fixed in or on a catheter by any suitable method. For example, in some variations one or more magnetic elements may be embedded in, adhered to, or friction-fit within a catheter.

Each magnetic element included in the catheters described here may have any suitable size and shape. For example, each magnetic element may be cylindrical, semi-cylindrical, tube-shaped, box-shaped, planar, spherical, or the like. Generally, the dimensions of the magnetic elements may be constrained by size of the catheters carrying the magnetic elements, which in turn may be constrained by the anatomical dimensions of the vessels through which the catheters described here may be advanced. For example, if the catheter is to be advanced through a blood vessel having an internal diameter of about 3 mm, it may be desirable to configure any magnetic element to have an outer diameter of less than about 3 mm to reduce the risk of injury to vessel walls during advancement and manipulation of the catheter. Each magnetic element may have any suitable length (e.g., about 5 mm, about 10 mm, about 15 mm, about 20 mm, or the like), although it should be appreciated that in some instances longer magnets may limit the flexibility of the catheter to maneuver through tissue.

As mentioned above, when two catheters each comprise one or more magnetic elements, the magnetic elements of the catheters may produce an attractive force between the catheters which may act to pull the catheters into closer approximation. Once the first and second catheters have been positioned, the attractive force may also act to maintain the relative positioning between the catheters. When the first and second catheters are placed in respective blood vessels, tissue positioned between the blood vessels may limit the ability of the first and second catheters to be brought toward each other. Accordingly, it may be desirable to maximize the attractive force between the first and second catheters in order to help the first and second catheters to displace tissue between the blood vessels.

In some variations, in order to increase the attractive force between two catheters, it may be desirable to focus the strength of a magnetic field generated by a magnetic element or array of magnetic elements. In some instances, it may be desirable to focus the magnetic field produced by a magnetic element or array of magnetic elements such that the strength of the magnetic field is greater on one side of the magnet than the strength of the magnetic field produced on an opposite side of the magnet. In other words, these locally-concentrated magnetic elements may have a magnetic flux distribution that is greater on one side of the magnetic element than on an opposite side of the magnetic element. In some variations, one or more magnetic elements may be configured to have a substantially one-sided flux distribution. In these variations, the one or more magnetic elements may be configured such that the magnetic elements produce a magnetic field on a first side of the magnetic elements, but do not produce a significant magnetic field on a second side of the magnetic elements. Accordingly, the flux distribution of the magnetic elements is limited to the first side of the magnetic elements, also known as a "one-sided flux" arrangement. While a one-sided flux arrangement ideally produces no flux distribution on the second side of the magnetic elements, it should be appreciated that in practice a one-sided flux arrangement may produce negligible stray field on the second side of the magnetic elements (e.g., due to imperfections in the machining process or due to assembly of individually magnetic elements). When one or more magnetic elements are configured as a one-sided flux arrangement, the strength of the magnetic field produced on the first side of the magnetic elements may be twice the strength of a magnetic field produced by a standard magnet of a similar size, shape, and construction. In other variations, one or more magnetic elements may be configured to produce a magnetic field that is stronger on a first side of the magnetic elements than it is on a second side of the magnetic elements opposite the first side of the magnetic elements, but to a lesser extent than a one-sided arrangement. For example, in some variations, one or more magnetic elements may be configured to generate a magnetic field having a flux distribution on a first side of the magnetic elements that is about 1.5 times as much as the flux distribution on a second side of the magnetic elements, about 2 times as much as the flux distribution on a second side of the magnetic elements, about 3 times as much as the flux distribution on a second side of the magnetic elements, about 5 times as much as the flux distribution on a second side of the magnetic elements, or the like.

Generally, to create a focused magnetic field as described immediately above, a catheter may comprise one or more magnets having a magnetization pattern, such as a Halbach array, configured to generate the desired magnetic field. Generally, the one or more magnets may comprise an array of regions, where each region has a specific polarity. The direction of the polarity of each respective region may be selectively arranged to produce a pattern of magnetic polarities, which may alter overall magnetic field produced by the array. The array may be formed from one or multiple discrete magnets, as will be discussed in more detail below.

Figure 2A:
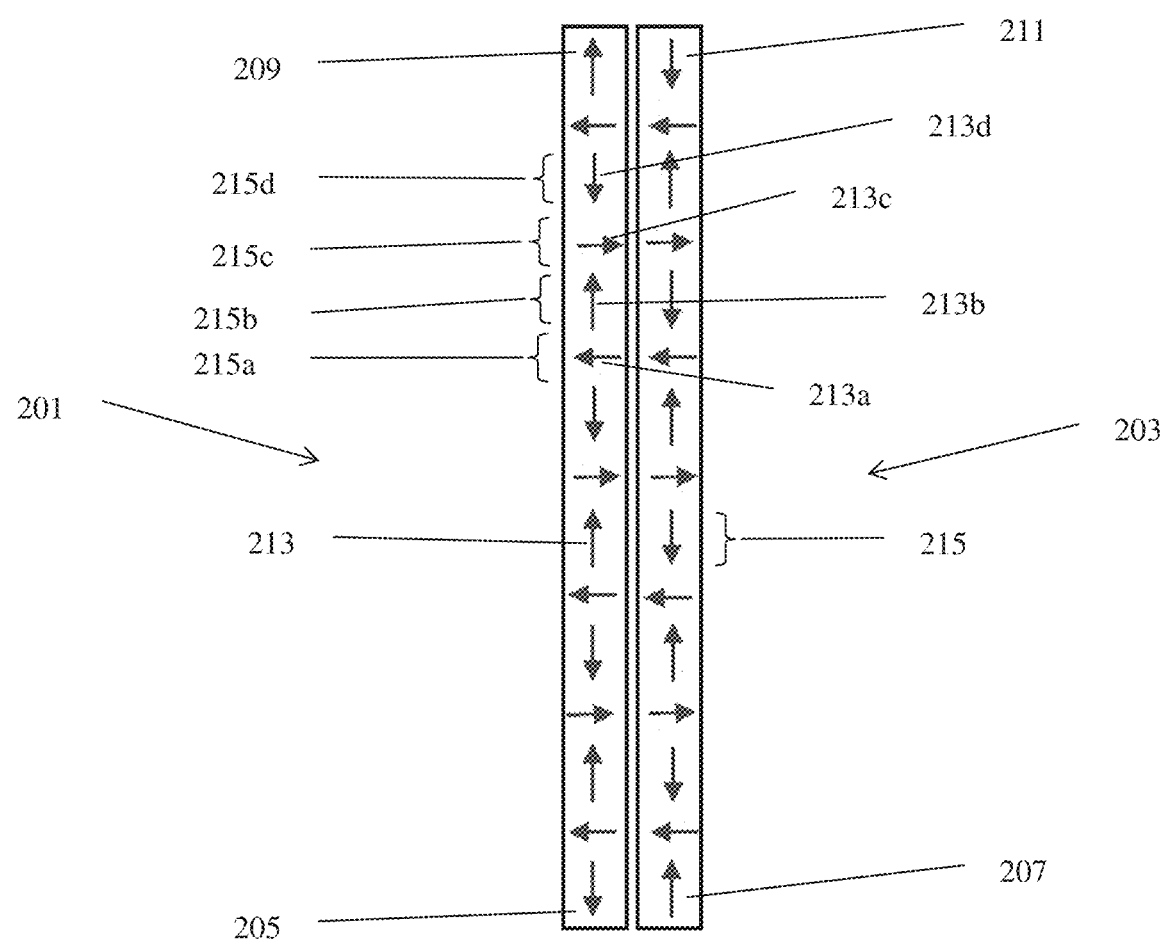
FIGS. 2A-2B, 3A-3B, and 4 are illustrative depictions of variations of magnetic arrays having magnetization patterns suitable for use with the catheters described here.

FIG. 2A depicts one variation of a pair of magnetic arrays which may be configured to produce focused magnetic fields. Shown there are a first magnetic array (201) and a second magnetic array (203). The first magnetic array (201) may be configured to produce a magnetic field (not shown) that is stronger on a first side (i.e., the right side of the array as depicted in FIG. 2A) of the array than on an opposite second side (i.e., the left side of the array as depicted in FIG. 2A) of the array. The second magnetic array (203) may be configured to produce a magnetic field (not shown) that is stronger on a first side (i.e., the left side of the array as depicted in FIG. 2A) of the array than on an opposite second side (i.e., the right side of the array as depicted in FIG. 2A) of the array. When the first magnetic array (201) and second magnetic array (203) are positioned such that the first side of the first magnetic array (201) faces the first side of the second magnetic array (203) (such as shown in FIG. 2A), the magnetic field produced by the first magnetic array (201) may attract the second magnetic array (203) toward the first magnetic array (201), while the magnetic field produced by the second magnetic array (203) may in turn attract the first magnetic array (201) toward the second magnetic array (203). Because the fields produced by these magnetic arrays are localized, the attractive force provided by the arrays may be greater than those produced by other similarly-sized magnets.

Generally, each of the magnetic arrays (201) and (203) are divided into a plurality of regions (215), wherein each region has a magnetic polarity (represented by arrows (213)). The direction of the polarities of the regions (215) may change from one region to the next according to a magnetization pattern. For example, in the variation of the first magnetic array (201) depicted in FIG. 2A, the first magnetic array (201) may have a proximal end (205) and a distal end (209), and may have a magnetization pattern in which the polarity of each region is rotated 90 degrees clockwise from the polarity of an immediately preceding region when looking at the magnetization pattern in a proximal-to-distal direction. Four regions (215a), (215b), (215c), and (215d) of the first magnetic array (201) having respective polarities (213a), (213b), (213c), and (213d) are marked in FIG. 2A to help illustrate this pattern. As shown there, region (215a) has a polarity (213a) in a first direction (e.g., to the left, as shown in FIG. 2A). Region (215b), the next region distal to region (215a), has a polarity (213b) in a direction that is rotated 90 degrees clockwise relative to the polarity (213a) of region (215a) (e.g., toward the distal end (209) as depicted in FIG. 2A). Similarly, region (215c), the next region distal to region (215b), has a polarity (213c) in a direction that is rotated 90 degrees clockwise relative to the polarity (213b) of region (215b) (e.g., toward the right as depicted in FIG. 2A). Finally, region (215d), the next region distal to region (215c), has a polarity (213d) in a direction that is rotated 90 degrees clockwise relative to the polarity (213c) of region (215c) (e.g., toward the proximal end (205) as depicted in FIG. 2A). This pattern may be continued along the length of the first magnetic array (201). In the first magnetic array (201) shown in FIG. 2A, each region (215) may produce a magnetic field, but the alternating polarities between adjacent regions may at least partially cancel out the magnetic field produced on the left side of the magnetic array (201) while augmenting the magnetic field produced on the right side of the magnetic array (201). It should be appreciated that the magnetic arrays described here having magnetization patterns may have any suitable number of regions (e.g., two or more regions, three or more regions, four or more regions, five or more regions, ten or more regions, or the like).

Similarly, in the variation of the second magnetic array (203) depicted in FIG. 2A, the second magnetic array (203) may have a proximal end (207) and a distal end (211), and may have a magnetization pattern in which the polarity of each region is rotated 90 degrees from the polarity of an immediately preceding region when looking at the magnetization pattern in a proximal-to-distal direction. In the second magnetic array (203), the polarity of each region is rotated 90 degrees counter-clockwise from an immediately preceding region, as opposed to clockwise as in the first magnetic array (201). In these instances, each region (215) may again produce a magnetic field, but the alternating polarities between adjacent regions may at least partially cancel out the magnetic field produced on the right side of the magnetic array (203) while augmenting the magnetic field produced on the left side of the magnetic array (203).

While the first and second magnetic arrays (201) and (203) are shown in FIG. 2A as having regions that each have a length equal to the width of the region, it should be appreciated that in some or all of the regions of the magnetic arrays described here may have a length that is different than the width of the region. For example, in some variations some or all of the regions of a magnetic array may have lengths greater than their widths. In other variations, some or all of the regions of a magnetic array may have lengths shorter than their widths. Additionally, while each of the regions (215) of the first and second magnetic arrays (201) and (203) are shown in FIG. 2A as having the same length, it should be appreciated that different regions may have different lengths.

Figure 2B:
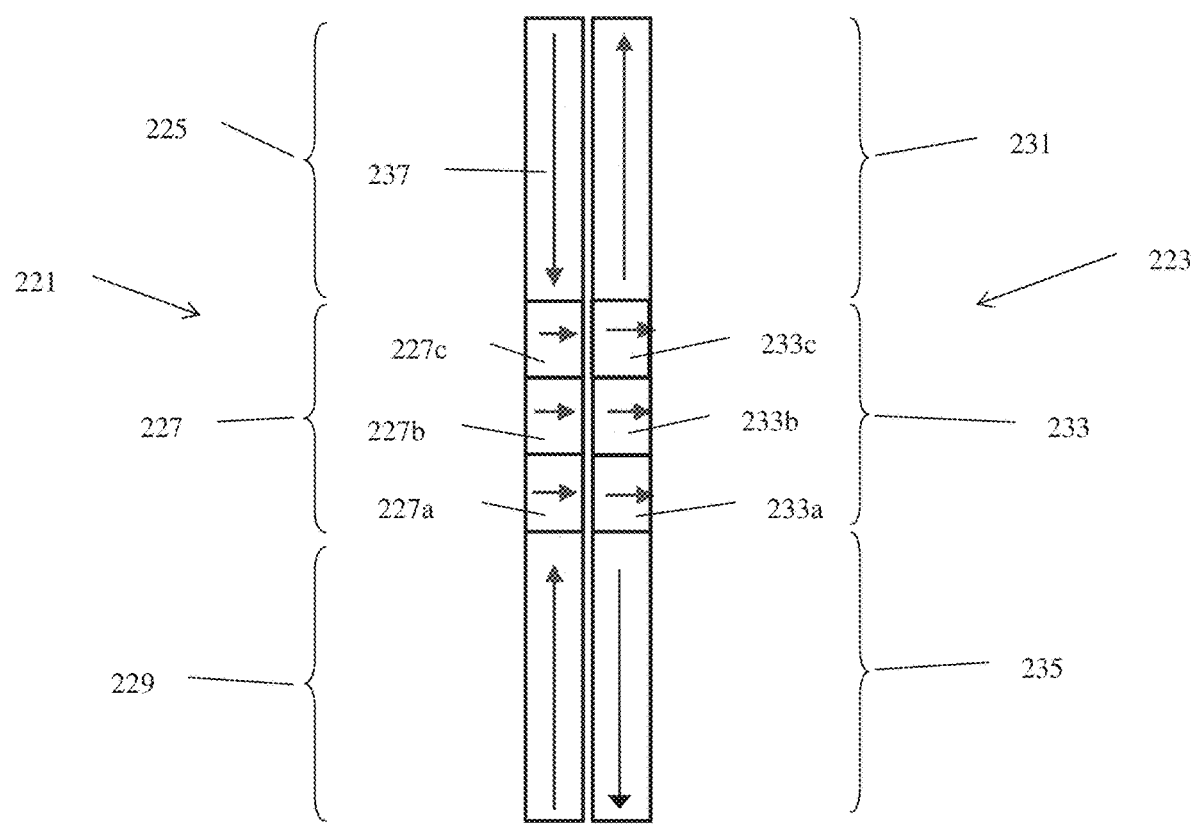

The magnetic arrays described here having magnetization patterns may be formed from one or more magnets. For example, in some variations, a magnetic array may comprise a single magnet. In these variations, the magnet may be magnetized such that it has distinct regions with differing polarities. For example, in the some instances, the first magnetic array (201) and/or the second magnetic array (203) may be formed from a single magnet, such that each region of the magnet is magnetized with a specific polarization. In other variations, a magnetic array may comprise a plurality of magnets. In these variations, each region of the array may be formed from a single magnet, or from multiple magnets. For example, FIG. 2B shows a portion of a first magnetic array (221) and a second magnetic array (223). The first magnetic array (221) is shown as having a first region (225), a second region (227), and a third region (229), wherein each region has a polarity (represented by arrows (237)) that is rotated 90 degrees clockwise relative to that of the immediately preceding region when looking at the magnetization pattern in a proximal-to-distal direction, similar to the magnetization pattern of the first magnetic array (201) described above with respect to FIG. 2A. Similarly, the second magnetic array (223) is shown as having a first region (231), a second region (233), and a third region (235), wherein each region has a polarity that is rotated 90 degrees counter-clockwise relative to that of the immediately preceding region when looking at the magnetization pattern in a proximal-to-distal direction, similar to the magnetization pattern of the second magnetic array (203) described above with respect to FIG. 2A. As shown in FIG. 2B, the first and third regions (225) and (229) of the first magnetic array (221) may each be formed from a single magnet, while the second region (227) may be formed from a plurality of individual magnets (e.g., three magnets, which are labeled in FIG. 2B as (227a), (227b), and (227c)). Similarly, the first and third regions (231) and (235) of the second magnetic array (223) may each be formed from a single magnet, while the second region (233) may be formed form a plurality of individual magnets (e.g., three magnets, which are labeled in FIG. 2B as (233a), (233b), and (233c)). While the second regions (227) and (233) are shown as each comprising three magnets, an individual region may be made up of any suitable number of magnets (e.g., one, two, three, or four or more magnets).

Figure 3A:
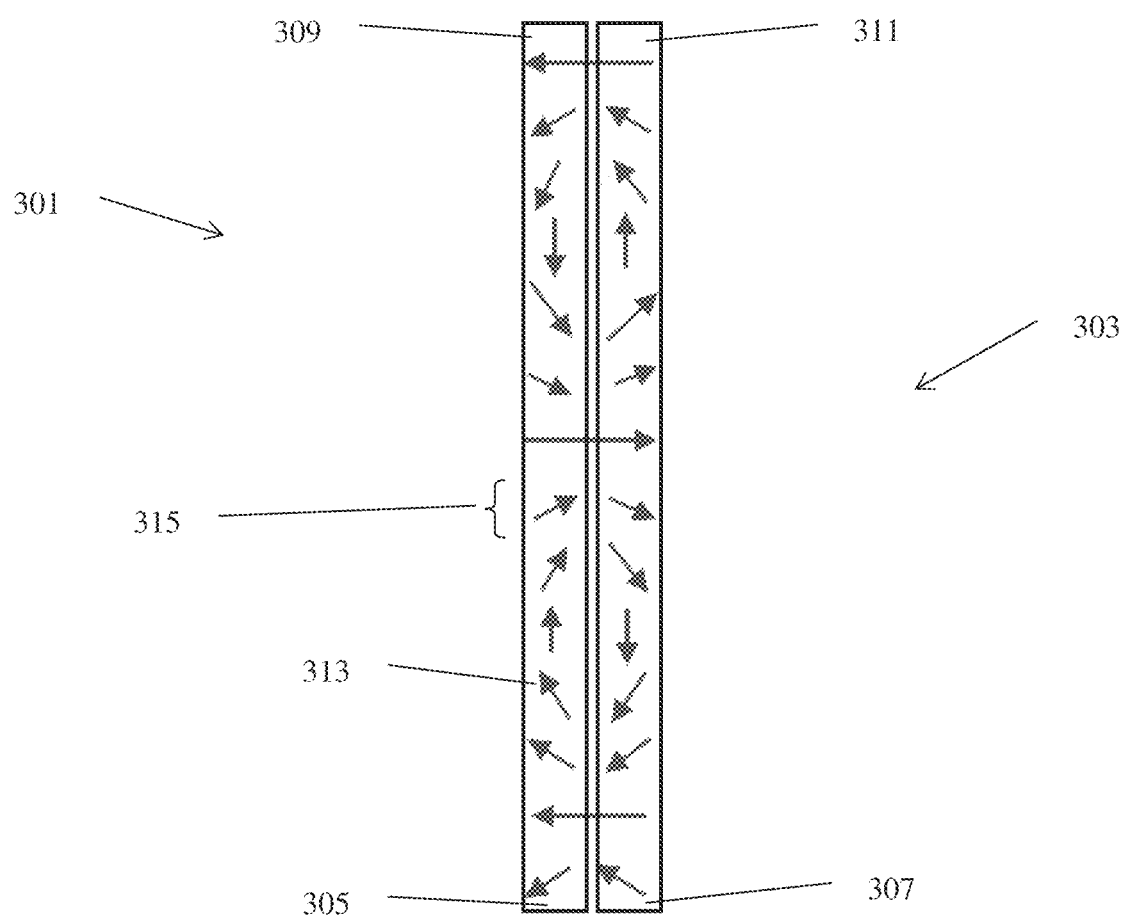

In the magnetization patterns depicted in FIGS. 2A and 2B above, the polarization of each region is shown as being either parallel or perpendicular to a longitudinal axis of the magnetic array. It should be appreciated, however, that in some variations, the polarities of the regions within a magnetization pattern may be positioned at any suitable angle. For example, in some variations, a magnetic array may comprise a plurality of regions where each region has a polarity that is rotated 90 degrees relative to an immediately preceding region, and wherein the polarity of each region is angled 45 degrees relative to the longitudinal axis of the magnetic array. Additionally, while the magnetic arrays described above have magnetization patterns in which each region has a polarity that is rotated 90 degrees relative to the polarity of an immediately preceding region, it should be appreciated that the angle between adjacent regions may be any suitable value. For example, in some variations, one or more magnetic arrays may have a magnetization pattern in which there is a 30 degree rotation between the polarities of adjacent regions. FIG. 3A shows one such variation of a pair of magnetic arrays. Shown there are a first magnetic array (301) having a proximal end (305) and a distal end (309) and a second magnetic array (303) having a proximal end (307) and a distal end (311). Each of the arrays may comprise a plurality of regions (315) each having a polarity (indicated by arrows (313)). The first magnetic array (301) may have a magnetization pattern in which the polarity of each region is rotated 30 degrees clockwise from the polarity of an immediately preceding region when looking at the magnetization pattern in a proximal-to-distal direction. Each region (315) of the first magnetic array (301) may produce a magnetic field, but the rotating polarities between adjacent regions may at least partially cancel out the magnetic field produced on the left side of the magnetic array (301) while augmenting the magnetic field produced on the right side of the magnetic array (301). Similarly, the second magnetic array (303) may have a magnetization pattern in which the polarity of each region is rotated 30 degrees counter-clockwise from the polarity of an immediately preceding region when looking at the magnetization pattern in a proximal-to-distal direction. Each region (315) of the second magnetic array (303) may produce a magnetic field, but the rotating polarities between adjacent regions may at least partially cancel out the magnetic field produced on the right side of the magnetic array (303) while augmenting the magnetic field produced on the left side of the magnetic array (303). As mentioned above, the magnetic arrays may be formed from a single magnet (e.g., a single piece of material) which may have regions with different of the magnet with different polarities as discussed above. In these variations, the polarity of the individual regions may be achieved by subjecting the magnet to a complex magnetic field-pattern to set the magnetic pattern of the magnetic arrays.

Figure 3B:
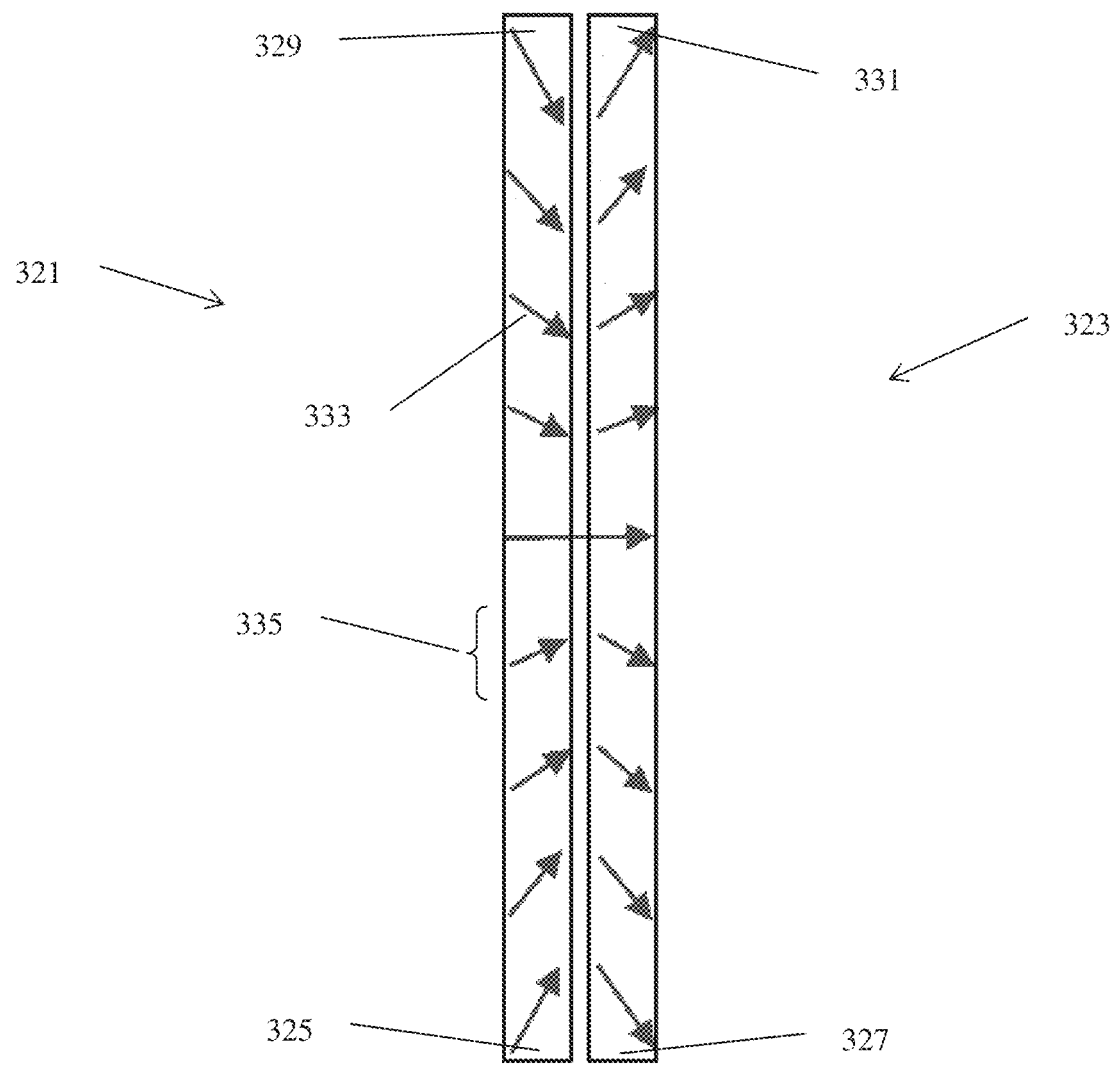

For example, in other variations, one or more magnetic arrays may have a magnetization pattern in which there is a 15 degree rotation between the polarities of adjacent regions. FIG. 3B shows one such variation of a pair of magnetic arrays. Shown there are a first magnetic array (321) having a proximal end (325) and a distal end (329) and a second magnetic array (323) having a proximal end (327) and a distal end (331). Each of the arrays may comprise a plurality of regions (335) each having a polarity (indicated by arrows (333)). The first magnetic array (321) may have a magnetization pattern in which the polarity of each region is rotated 15 degrees clockwise from the polarity of an immediately preceding region when looking at the magnetization pattern in a proximal-to-distal direction. Each region (335) of the first magnetic array (321) may produce a magnetic field, but the rotating polarities between adjacent regions may at least partially cancel out the magnetic field produced on the left side of the magnetic array (321) while augmenting the magnetic field produced on the right side of the magnetic array (321). Similarly, the second magnetic array (323) may have a magnetization pattern in which the polarity of each region is rotated 15 degrees counter-clockwise from the polarity of an immediately preceding region when looking at the magnetization pattern in a proximal-to-distal direction. Each region (335) of the second magnetic array (323) may produce a magnetic field, but the rotating polarities between adjacent regions may at least partially cancel out the magnetic field produced on the right side of the magnetic array (323) while augmenting the magnetic field produced on the left side of the magnetic array (323).

Figure 4:
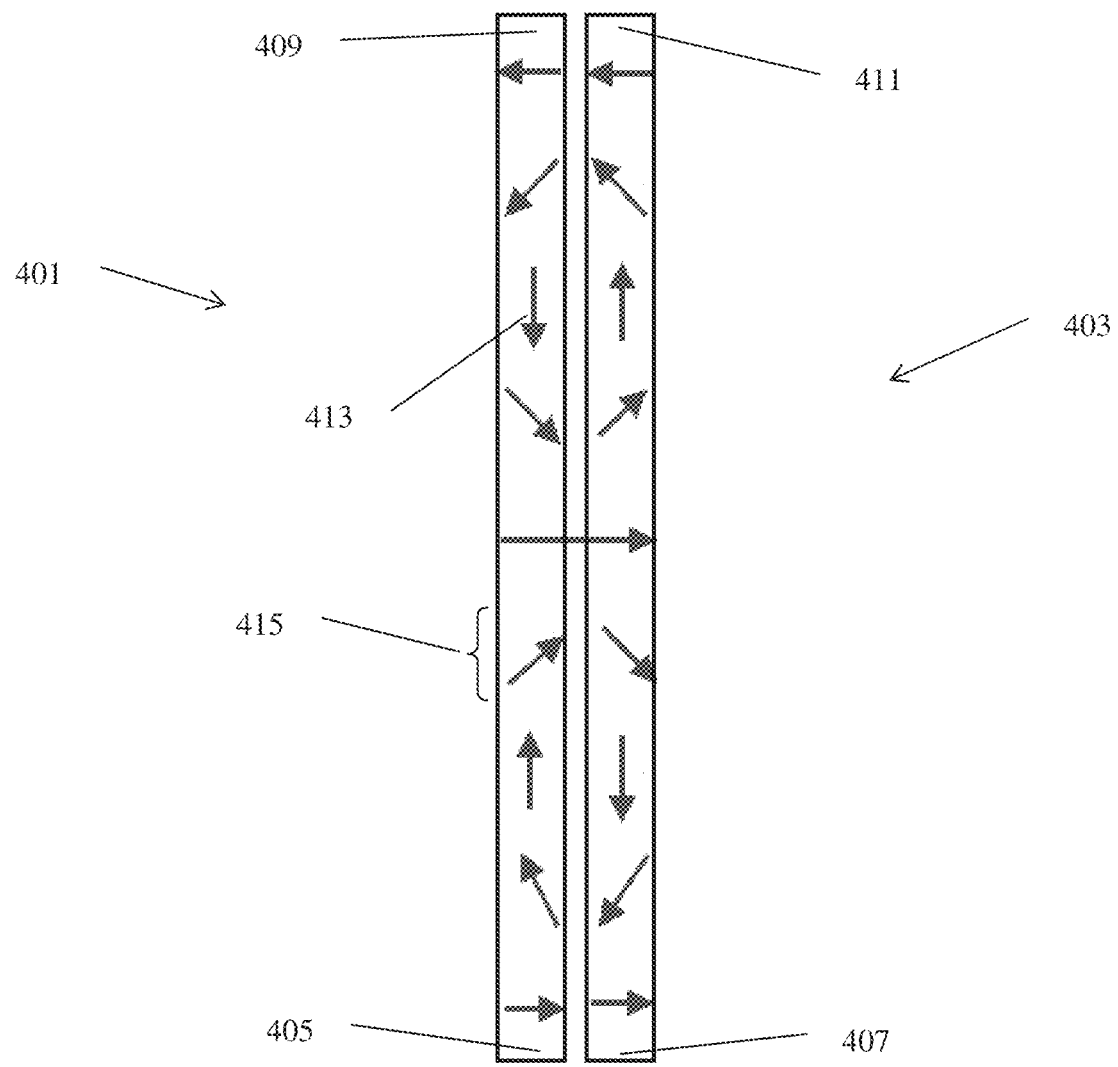

In still other variations, one or more magnetic arrays may have a magnetization pattern in which there is a 45 degree rotation between the polarities of adjacent regions. FIG. 4 shows one such variation of a pair of magnetic arrays. Shown there are a first magnetic array (401) having a proximal end (405) and a distal end (409) and a second magnetic array (403) having a proximal end (407) and a distal end (411). Each of the arrays may comprise a plurality of regions (415) each having a polarity (indicated by arrows (413)). The first magnetic array (401) may have a magnetization pattern in which the polarity of each region is rotated 45 degrees clockwise from the polarity of an immediately preceding region when looking at the magnetization pattern in a proximal-to-distal direction. Each region (415) of the first magnetic array (401) may produce a magnetic field, but the rotating polarities between adjacent regions may at least partially cancel out the magnetic field produced on the left side of the magnetic array (401) while augmenting the magnetic field produced on the right side of the magnetic array (401). Similarly, the second magnetic array (403) may have a magnetization pattern in which the polarity of each region is rotated 45 degrees counter-clockwise from the polarity of an immediately preceding region when looking at the magnetization pattern in a proximal-to-distal direction. Each region (415) of the second magnetic array (403) may produce a magnetic field, but the rotating polarities between adjacent regions may at least partially cancel out the magnetic field produced on the right side of the magnetic array (403) while augmenting the magnetic field produced on the left side of the magnetic array (403). As mentioned above, the magnetic arrays shown in FIG. 4 may be each be formed from a single magnet or from a plurality of individual magnetic elements.

The ability to generate locally concentrated magnetic fields may allow the catheters described here to increase the attractive force between the catheters when the size of the catheters (and the magnetic elements thereof) is otherwise constrained. Because the magnetic elements of the catheters described may be advanced into the body, the patient's anatomy may place constraints on the dimensions of the catheters and the magnetic elements, such as discussed.

Accordingly, a magnetic array which generates a local magnetic field may help to maximize the attractive force between two catheters, which may allow the catheters to overcome additional compliance and/or resistance (e.g., by tissue between the vessels) to help bring the catheters into apposition.

It should be appreciated that although the magnetic arrays discussed above with respect to FIGS. 2A-2B, 3A-3B, and 4 have been described as pairs, a catheter system may utilize any combination of magnetic arrays as described here. For example, when the systems described here comprise a first catheter and a second catheter, either the first and/or second catheter may have one or more magnetic elements that produce a locally-concentrated magnetic field. For example, in some variations, a first catheter of a system may comprise one or more magnetic elements that produce a locally-concentrated magnetic field. The first catheter may include any of the magnetic arrays discussed above with respect to FIGS. 2A-2B, 3A-3B, and 4. The second catheter may also comprise one or more magnetic elements that produce a locally-concentrated magnetic field, but need not. In variations where each of the first and second catheters include one or more magnetic elements that produce a locally-concentrated magnetic field, the catheters may comprise any combination of the magnetic arrays described above with respect to FIGS. 2A-2B, 3A-3B, and 4. For example, in some variations, the first catheter may comprise a first magnetic array having a magnetization pattern having a first angle between the polarities of adjacent regions, and the second catheter may comprise a second magnetic array having a second angle between the polarities of adjacent regions. In some variations, the first angle of the first magnetic array may be a clockwise rotation between adjacent regions in a proximal-to-distal direction, while the second angle of the second magnetic array may be a counter-clockwise rotation between adjacent regions in a proximal-to-distal direction. In other variations, both the first angle of the first magnetic array and the second angle of the second magnetic array may be a clockwise rotation (or both may be a counter-clockwise rotation) between adjacent regions in a proximal-to-distal direction. The first angle and second angle may be any suitable value, such as described in more detail above, and the first angle may be the same as or different than the second angle.

Magnetic Control Device

In another embodiment, the systems described may comprise a magnetic control device. This magnetic control device may be positioned externally to the body, and may provide one or more magnetic forces to one or more catheters positioned in the body. Generally, the magnetic control device may comprise a magnet configured to increase the attractive force between two catheters to help bring the catheters toward each other.

Figure 5A:
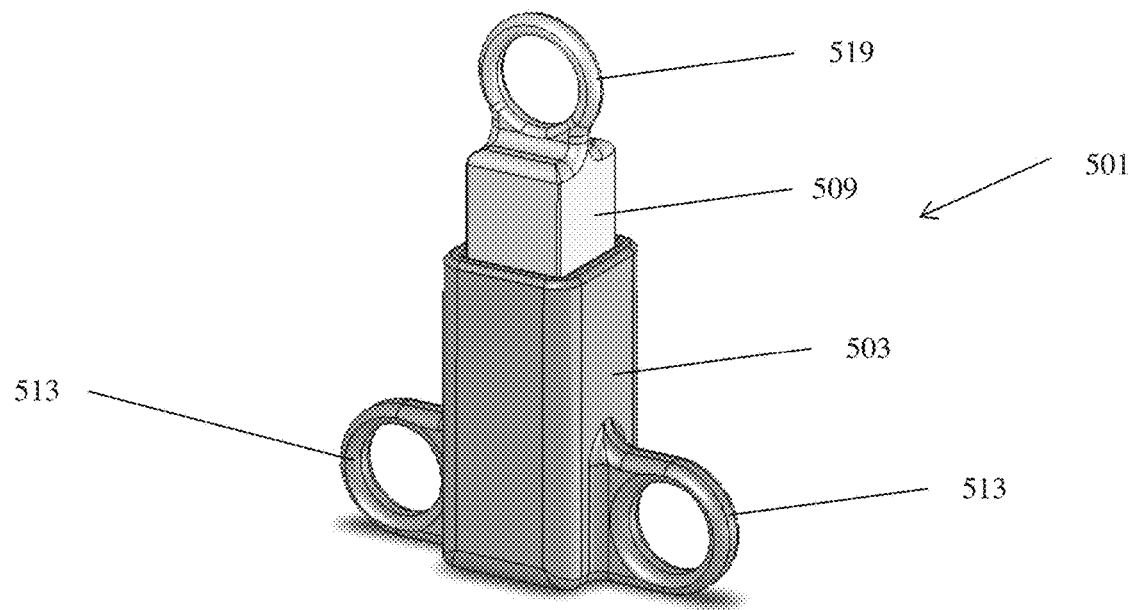
FIGS. 5A-5B are illustrative depictions of a perspective view and a cross-sectional side view, respectively, of a variation of a magnetic control device as described here.
Figure 5B:
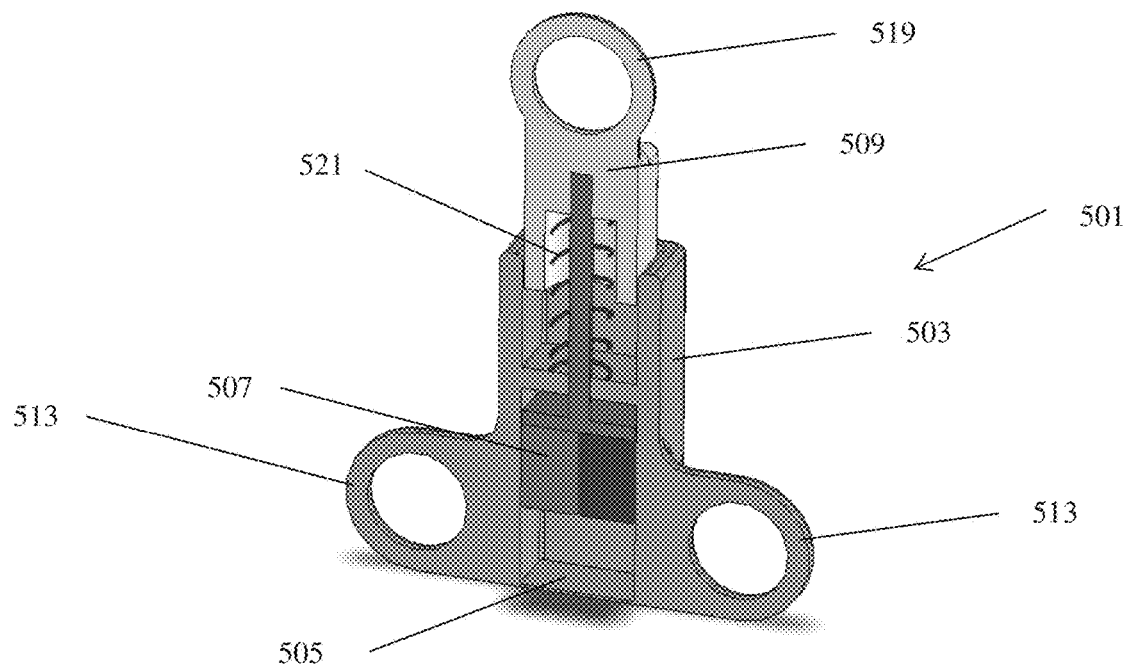

FIGS. 5A and 5B show one embodiment of a magnetic control device as described here. FIGS. 5A and 5B depict a perspective view and a cross-sectional perspective view, respectively, of the magnetic control device (501). As shown there, the magnetic control device (501) may comprise a housing (503) having a distal contact surface (505), a magnet (507) moveable relative to the housing (503), and a control element (509) for manipulating the magnet (507). In some variations, the magnetic control device (501) may comprise a spring (521) or other structure configured to bias the magnet (507) toward a specific position, as will be described in more detail below, but need not.

Generally, the magnet (507) of the magnetic control device (501) may be at least partially housed within the housing (503). The magnet (507) may be moveable relative to the housing (503) (as will be described below), and may be configured to increase the attractive force between two catheters that may be positioned in the body when the magnet (507) is positioned near the catheters. Because the magnet (507) is configured to be positioned external to the body, the magnet (507) may not be subject to the same size constraints as the magnetic elements of the catheters described here.

Figure 6A:
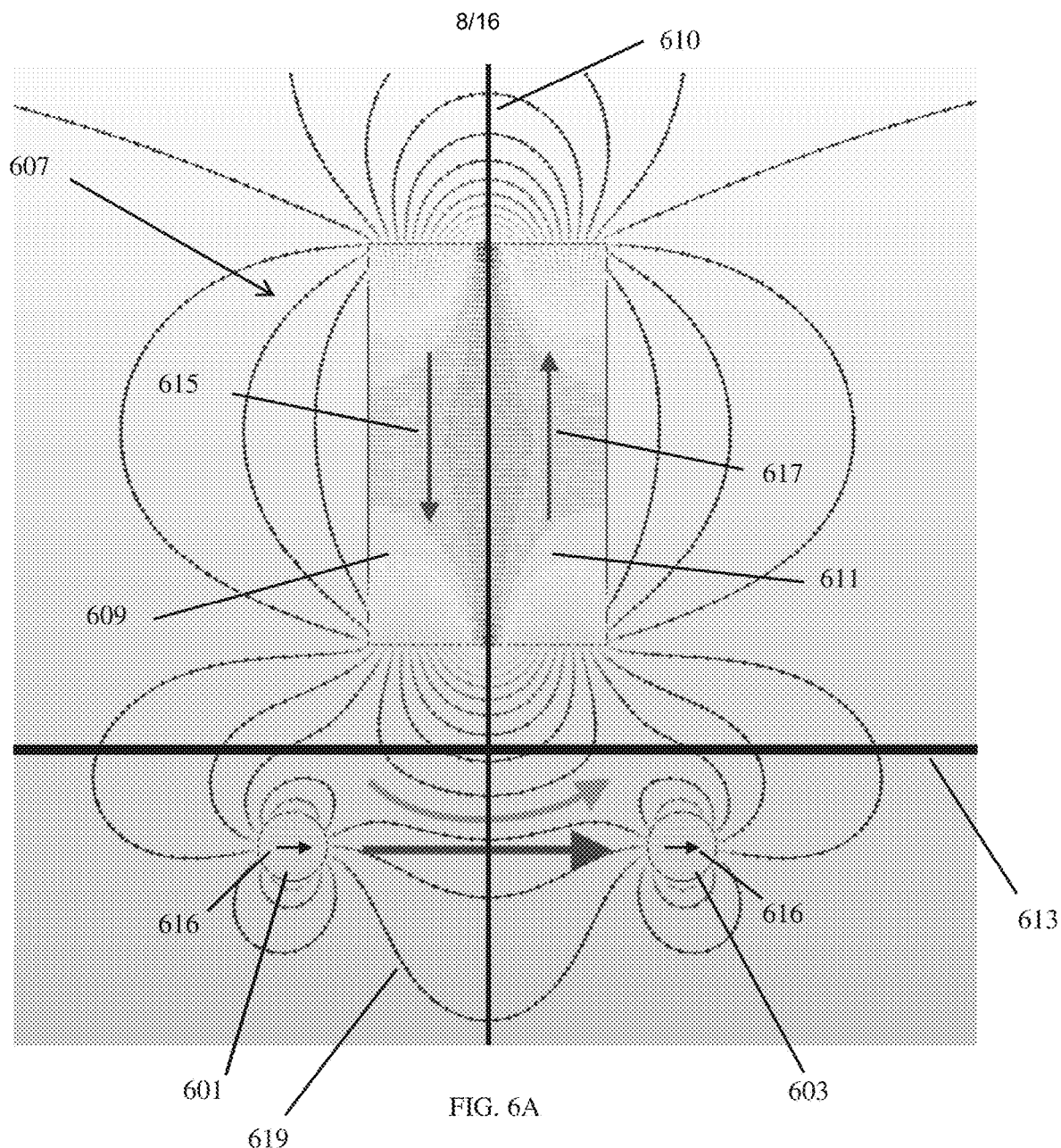
FIGS. 6A-6B, and 7-10 are illustrative depictions of variations of magnetic arrays having magnetization patterns suitable for use with magnetic control devices described here.

The magnet (507) of the magnetic control device may include an arrangement of one or more individual magnets, which may be configured to generate any suitable magnetic field. For example, FIGS. 6A-6B and 7-10 illustrate variations of magnetic arrangements that may be suitable for use with the magnetic control devices described here. FIG. 6A shows one variation in which a magnetic arrangement (607) may comprise a first magnetic element (609) positioned on a first side of a centerline (610), and a second magnetic element (611) positioned on the other side of the centerline (610) and attached to the first magnetic element (609) such that the polarity (indicated by arrow (615)) of the first magnetic element (609) is opposite the polarity (indicated by arrow (617)) of the second magnetic element (611). The magnetic arrangement (607) may create a magnetic field (represented in FIG. 6A by field lines (619)), which may be configured to pull magnetic elements toward the centerline (610) of the magnetic arrangement (607).

For example, when a first catheter (601) and a second catheter (603) are positioned in the body beneath the surface of the skin (represented in FIG. 6A as line (613)), the magnetic arrangement (607) may be positioned near the skin (613) such that the centerline (610) passes between the first catheter (601) and the second catheter (603). For example, when the first and second catheters are positioned in a plane substantially parallel to the skin (613), this may include positioning the magnetic arrangement (607) such that the centerline (610) is substantially perpendicular to the skin (613). The first and second catheters (601) and (603) may each comprise one or more magnetic elements (not shown), which may be responsive to the magnetic field produced by the magnetic arrangement (607). For example, in some variations the first and second catheters (601) and (603) include magnetic elements each having a polarity (indicated in FIG. 6A by arrows (616)) such that the magnetic field produced by the magnetic arrangement (607) may pull each of the first and second catheters (601) and (603) toward the centerline (610). Since the centerline is positioned between the first and second catheters, this may move the catheters toward each other to bring them in closer approximation.

Figure 6B:
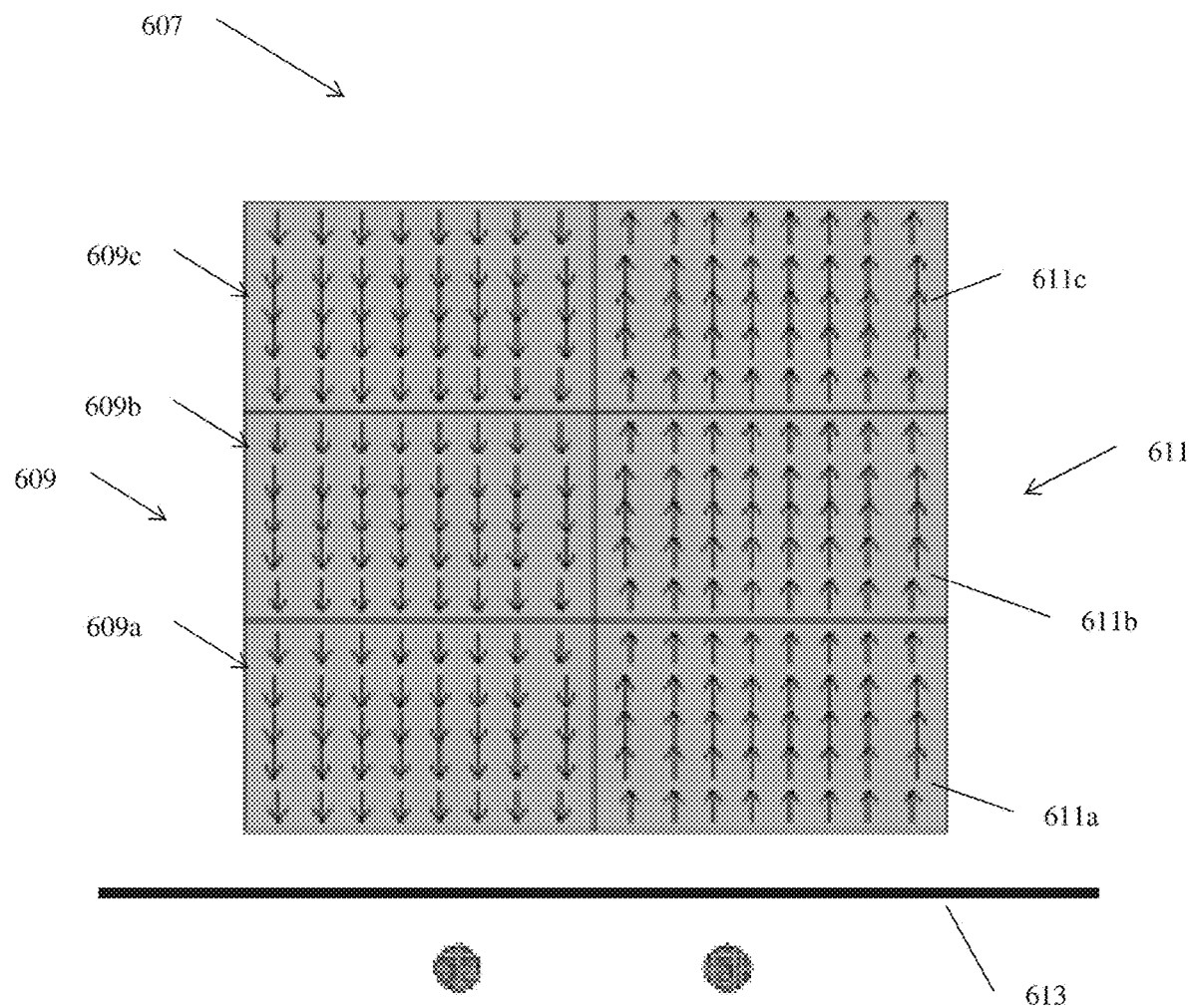

Each of the first magnetic element (609) and the second magnetic element (611) may be formed from one or more individual magnets. For example, in the variation of the magnetic arrangement (607) depicted in FIG. 6A, the first magnetic element (609) may be formed from a single magnet and the second magnetic element (611) may be formed from a single magnet. In other variations, one or more of the magnetic elements may be formed from multiple individual magnets. For example, FIG. 6B depicts a variation of the magnetic array (607) of FIG. 2A, except that the first magnetic element (609) is formed from three individual magnets (labeled as (609*a*), (609*b*), and (609*c*)) and the second magnetic element (611) is formed from three individual magnets (labeled as (611*a*), (611*b*), (611*c*)). While each of the first and second magnetic elements is shown in FIG. 2B as being formed from three individual magnets, it should be appreciated that the magnetic elements may be formed from any suitable number of individual magnets (e.g., one, two, three, or four or more magnets).

The magnetic array (607) may have any suitable dimensions. For example, the magnet array may have any suitable height, such as for example, between about 5 mm and about 25 mm, between about 10 mm and about 20 mm, or the like. Similarly, the array may have any suitable width, such as, for example, between about 5 mm and 35 mm, between about 8 mm and 28 mm, between about 10 mm and about 20 mm, or the like. The array may further have any suitable depth, such as, for example, between about 5 mm and about 40 mm, about 8 mm and about 28 mm, between about 10 mm and about 20 mm, or the like. While the variation of magnetic array (607) shown in FIG. 6A has a height that is greater than its width, in some instances the width of magnet (607) may be greater than or equal its height.

Figure 7:
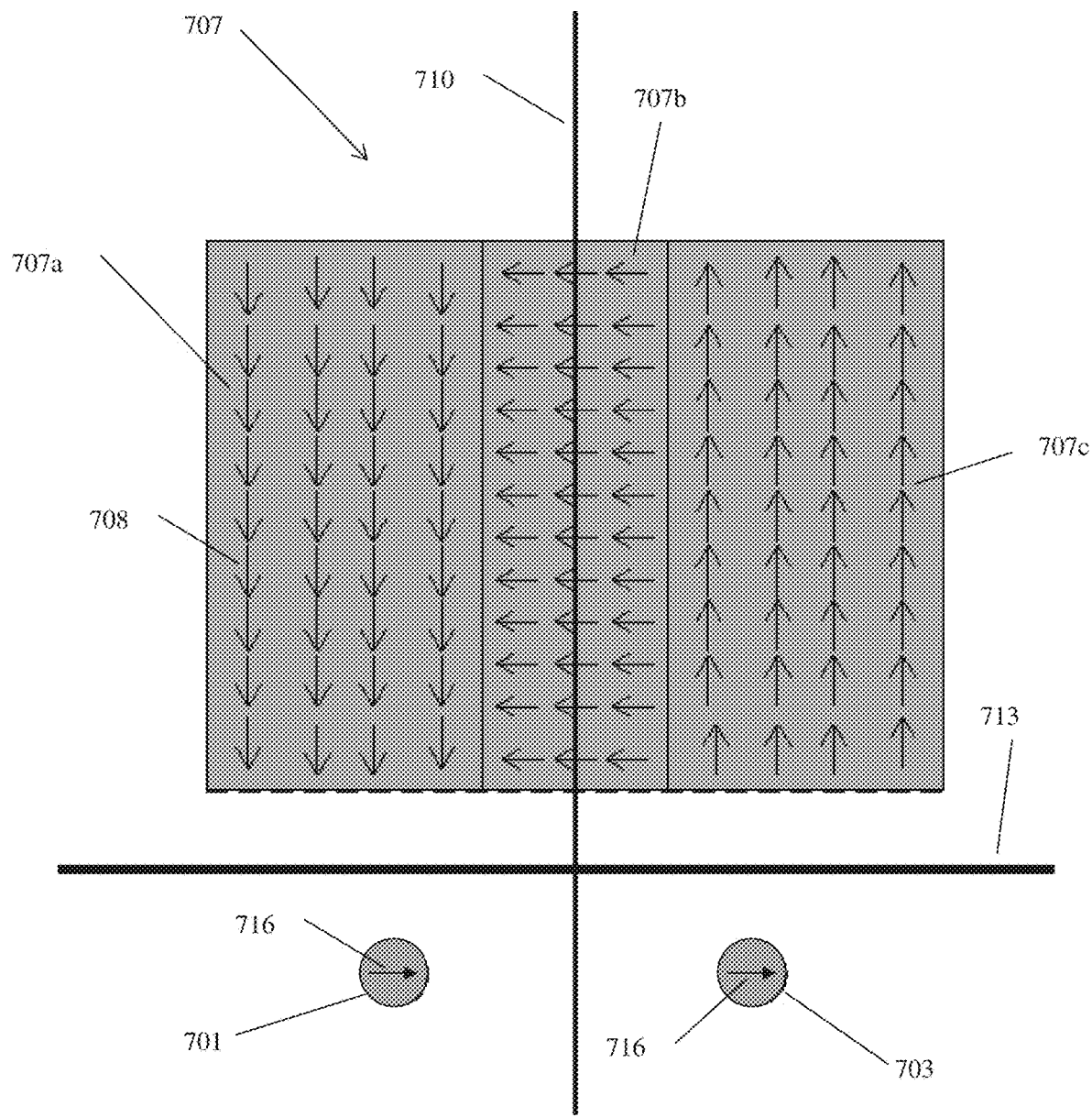

In other embodiments, the magnetic array may have a magnetization pattern which may generate a locally-concentrated magnetic field on one side of the array. For example, FIG. 7 illustrates a magnetic array (707) comprising a centerline (710) and a three-region magnetization pattern. Specifically, the magnetic array (707) may comprise three regions (707a), (707b), (707c), where the polarity (indicated in FIG. 7 by arrows (708)) of each region in magnetic array (707) is rotated ninety degrees relative to adjacent regions. In the variation of the magnetic array (707) shown in FIG. 7, the polarity of the left region (707a) may be in a first direction (e.g., parallel to the centerline (710)), the polarity of the middle region (707b) may be rotated ninety degrees clockwise from that of the left region (707a) (e.g., in a direction perpendicular to the centerline (710)), and the polarity of the right region (707c) may be rotated ninety degrees clockwise from that of the middle region (707b) (e.g., in a direction parallel to the centerline (710), but opposite the first direction). In these variations, the magnetic array (707) may produce a stronger magnetic field on one side of the magnetic array (707) (e.g., the bottom side of the array (707) as shown in FIG. 7) than on an opposite side of the array (707) (e.g., the top side of the array (707) as shown in FIG. 7). The magnetic field created by the magnetic array (707) may be configured to pull magnetic elements toward the centerline (710) of the magnetic array (707).

For example, when a first catheter (701) and a second catheter (703) are positioned in the body beneath the surface of the skin (represented in FIG. 7 as line (713)), the magnetic arrangement may be positioned near the skin (713) such that the centerline (710) passes between the first catheter (701) and the second catheter (703). For example, when the first and second catheters are positioned in a plane substantially parallel to the skin (713), this may include positioning the magnetic arrangement (707) such that the centerline is substantially perpendicular to the skin (713). The first and second catheters (701) and (703) may each comprise one or more magnetic elements (not shown), which may be responsive to the magnetic field produced by the magnetic arrangement (707). For example, in some variations the first and second catheters (701) and (703) include magnetic elements each having a polarity (indicated in FIG. 7 by arrows (716)) such that the magnetic field produced by the magnetic arrangement (707) may pull each of the first and second catheters (701) and (703) toward the centerline (710). Since the centerline is positioned between the first and second catheters, this may move the catheters toward each other to bring them in closer approximation. The magnetic array (707) may have any suitable dimensions, such as those described above with respect to the magnetic array (607) of FIGS. 6A and 6B.

In the magnetic array (707) shown in FIG. 7, the magnetic array may be formed from one or more magnets. In some instances, the magnetic array (707) may be formed from a single magnet such that the regions (707a), (707b), (707c) are portions of the same magnet having different polarities. In some variations, one or more of the regions (707a), (707b), (707c) may be formed by one or more separate magnets. In some of these variations, each of the regions is formed from one or more separate magnets. When a specific region is formed from one or more separate magnets, it should be appreciated that the region may be formed from a single magnet, or may be formed from a plurality of magnets, such as described in more detail above. Additionally, while only three regions are shown in the magnetic array (707), the magnetic array (707) may include any number of regions, wherein each region has a polarity that is rotated 90 degrees clockwise relative to a polarity of the adjacent region to its left.

Figure 8:
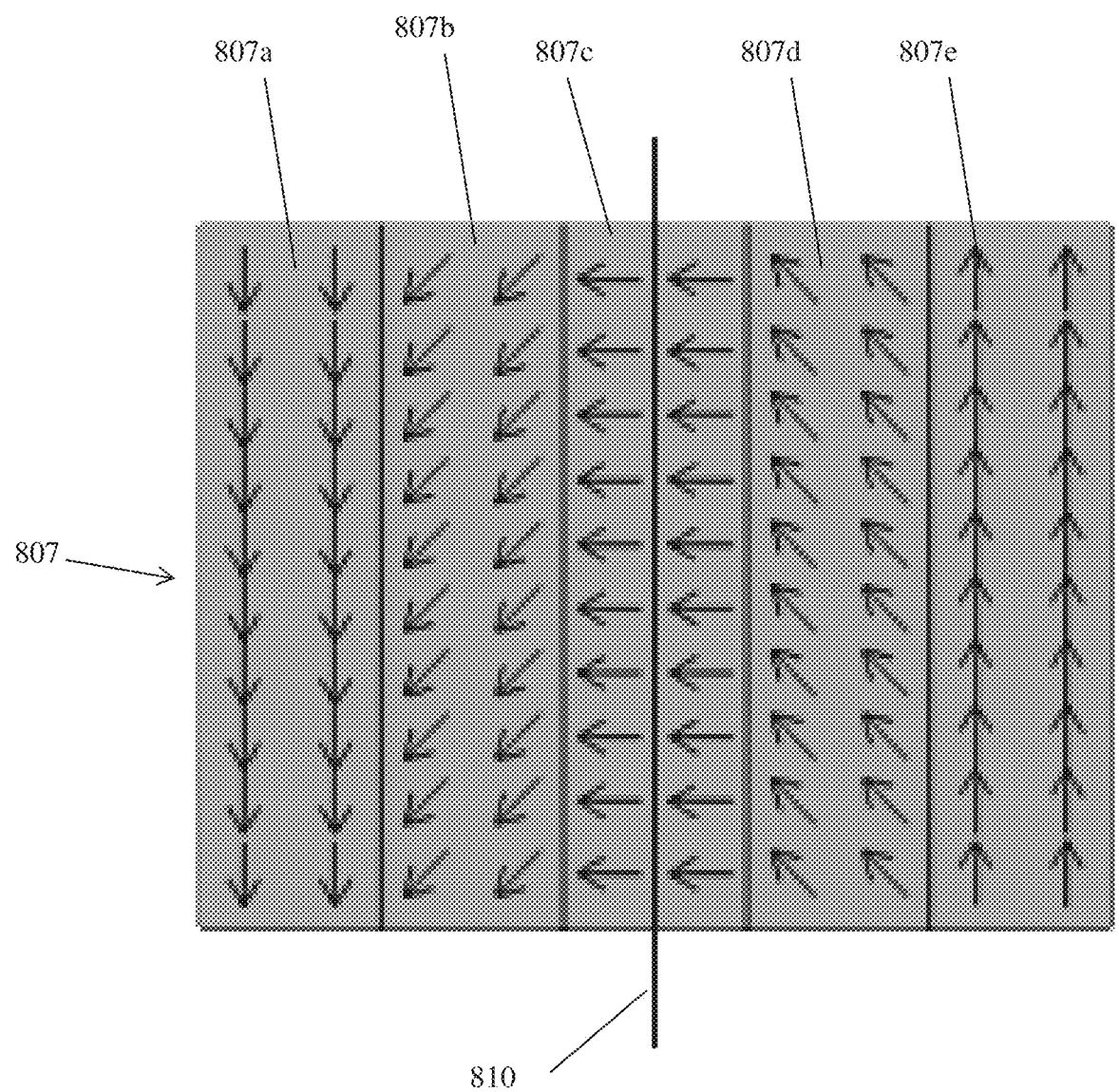

While the polarities in adjacent regions of the magnetic array (707) are rotated by 90 degrees, it should be appreciated that the magnetic arrays described here may have magnetization patterns in which adjacent regions have polarizations that are rotated any suitable angle (e.g., about 15 degrees, about 30 degrees, about 45 degrees, about 60 degrees or the like). For example, FIG. 8 shows one variation of a magnetic array (807) comprising five regions (807a), (807b), (807c), (807d), (807e), wherein each region is rotated forty-five degrees clockwise relative to the region on its left (when viewed from the orientation shown in FIG. 8). In these variations, the magnetic array (807) may produce a stronger magnetic field on one side of the magnetic array (807) (e.g., the bottom side of the array (807) as shown in FIG. 8) than on an opposite side of the array (807) (e.g., the top side of the array (807) as shown in FIG. 8). The magnetic field created by the magnetic array (807) may be configured to pull magnetic elements toward a centerline (810) of the magnetic array (807).

Figure 9:
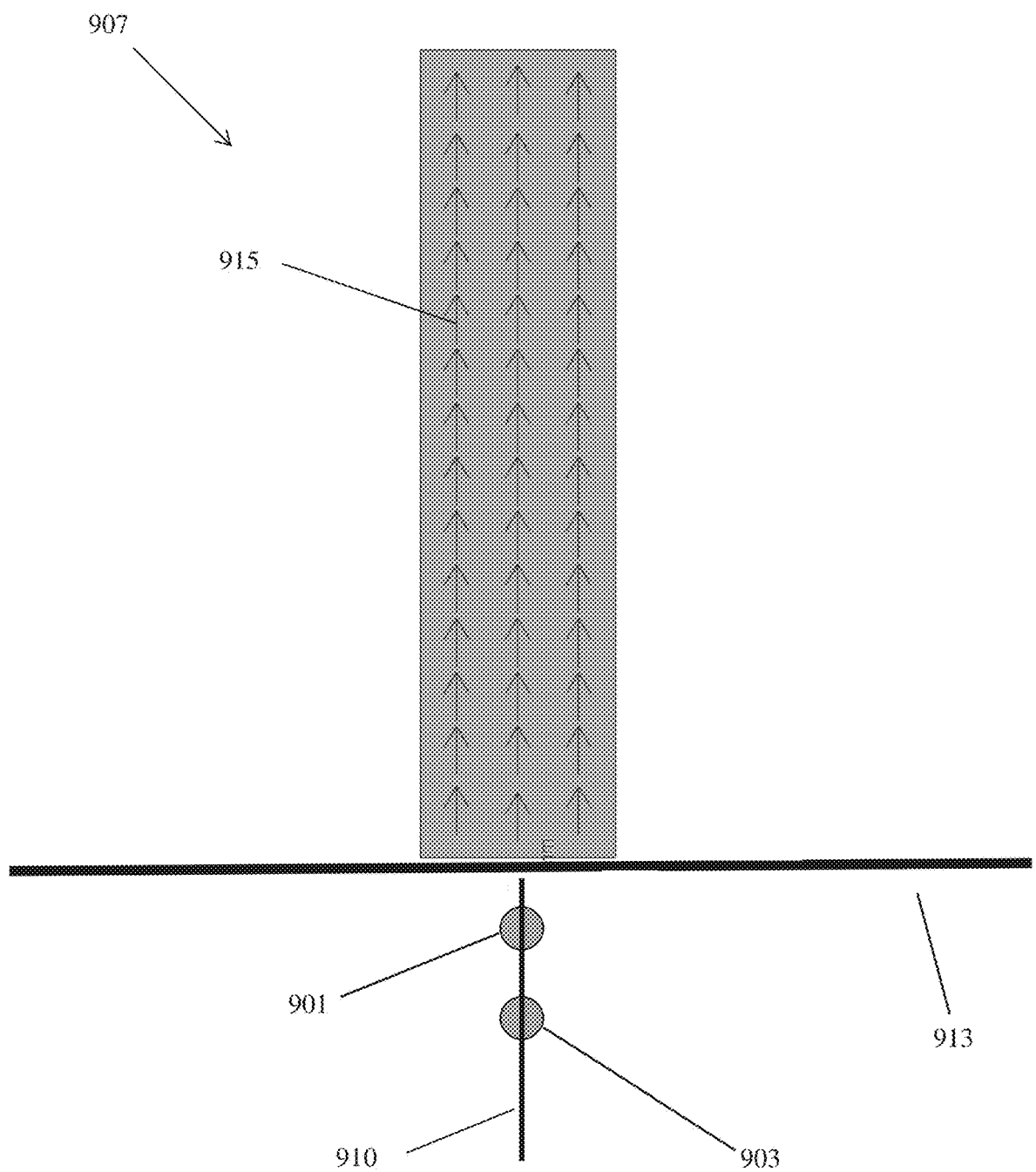

In instances when the two catheters positioned in the body lie in a plane that is substantially perpendicular to the surface of the skin, it may be difficult to position an external magnet such that a centerline of the magnet passes between the catheters. Accordingly, some of the magnets suitable for use with the magnetic control devices described here may be configured to bring the magnets in closer approximation when the catheters are aligned substantially perpendicular to a skin surface. For example, FIG. 9 shows a magnet (907) comprising a single polarity (indicated in FIG. 9 by arrows (915)), which may be configured to increase the attractive force between a first catheter (901) and a second catheter (903) that are positioned in a plane (910) that is substantially perpendicular to the skin surface (913). In these variations, the magnet (907) may be positioned near the skin surface (913) such that the direction of the polarity (915) of the magnet (907) is aligned with the plane (910) of the first and second catheters. In these instances, the magnet (907) may generate a magnetic field that may repulse the first and second catheters. Since the first catheter (901) is positioned closer to the magnet (907) than the second catheter (903), the force applied by the magnet (907) to the first catheter may be greater than the force applied by the magnet to the second catheter, which may cause the first catheter to move toward the second catheter. In other instances, the magnet (907) may be configured to attract both the first (901) and second catheter (903) toward the skin. Since the first catheter (901) is positioned closer to the skin, the tissue around the skin may provide greater resistance to movement toward than magnet than may be felt by the second catheter (903), which may draw the second catheter (903) toward the first catheter (901).

Figure 10:
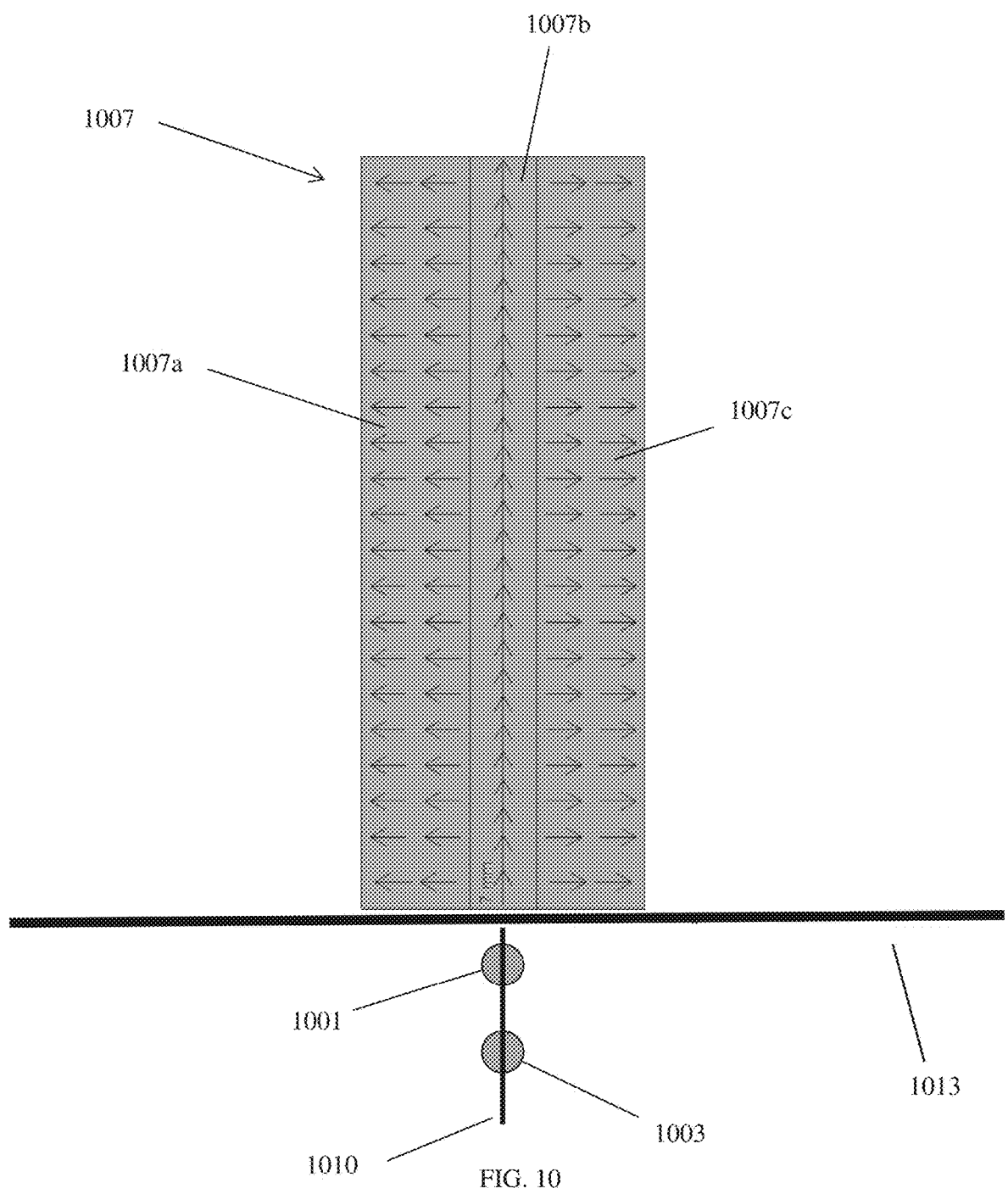

FIG. 10 illustrates another variation of a magnetic array (1007) configured to increase the attractive force between two catheters aligned substantially perpendicular to a skin surface. As shown there, the magnetic array (1007) may comprise a magnetization pattern comprising three regions (1007a), (1007b), (1007c), where the polarity of each region in magnetic array (1007) is rotated ninety degrees clockwise relative to the region on its left (when viewed from the orientation shown in FIG. 10). That is, the first region (1007a) may have a polarity in a first direction (e.g., to the left in the orientation shown in FIG. 10), the second region (1007b) may have a polarity that is rotated ninety degrees clockwise from the polarity of the first region (1007a) (e.g., toward the top of the magnet (1007) in the orientation shown in FIG. 10), and the third region (1007c) may have a polarity that is rotated ninety degrees from the polarity of the second region (1007b) (e.g., toward the right in the orientation shown in FIG. 10). In these variations, the rotating polarities of the regions may augment the magnetic field provided by a first side of the magnetic array (1007) (e.g., the bottom side in the orientation shown in FIG. 10), which may be configured to increase the attractive force between a first catheter (1001) and a second catheter (1003) that are positioned in a plane (1010) that is substantially perpendicular a skin surface (1013). In these variations, the magnet (1007) may be positioned near the skin (1013) such that the direction of the polarity of the second region (1007b) is aligned with the plane (1010) of the first and second catheters. In these instances, the magnetic array (1007) may generate a magnetic field that may repulse the first and second catheters. Since the first catheter (1001) is positioned closer to the magnetic array (1007) than the second catheter (1003), the force applied by the magnetic array (1007) to the first catheter may be greater than the force applied by the magnet to the second catheter, which may cause the first catheter to move toward the second catheter. In other variations, the magnetic array (1007) may be configured attract both the first (1001) and second (1003) catheters toward the skin of the patient, which may draw the second catheter (1003) toward the first catheter (1001) as discussed above with respect to the magnetic array (907) of FIG. 9. The individual regions of the magnetic array (1007) may be formed from one or more individual magnets, such as described in more detail above.

As with the magnetic arrays discussed above, the magnetic arrays (907) and (1007) shown in FIGS. 9 and 10 respectively may have any suitable dimensions, and specifically may have any suitable height (e.g., between about 5 mm and about 160 mm, between about 10 mm and about 150 mm, between about 20 mm and about 140 mm, between about 40 mm and about 120 mm, between about 75 mm and about 85 mm, etc.), width (e.g., between about 5 mm and about 50 mm, between about 10 mm and about 40 mm, between about 18 mm and about 25 mm), and depth (e.g., between about 5 mm and about 50 mm, between about 10 mm and about 40 mm, between about 18 mm and about 25 mm) While the variation of magnet (907) shown in FIG. 9 has a height that is greater than its width, in some instances the width of magnet (907) may be greater than its height.

Returning to FIGS. 5A and 5B, the magnetic control device (501) may comprise, in addition to the magnet (507), a housing (503) having a contact surface (505) a distal end of the housing that is configured to be placed against the skin. The housing (503) may at least partially house the magnet (507), and the magnet (507) may be moveable relative to the contact surface (505) of the housing to adjust the distance between the magnet (507) and the contact surface (505). In use, the contact surface (505) may be placed against a skin surface, and may act as a stop which may limit movement of one or more catheters or tissue relative to the magnet (507), as will be described in more detail below. The contact surface (505) may be formed from one or more rigid materials (e.g., a hard plastic or the like) or may be formed from one or more flexible materials.

As mentioned above, the magnetic control device (501) may comprise a control element (509) configured to selectively move the magnet (507) relative to the housing (503) and the contact surface (505). Specifically, the magnet (507) may be fixed to the control element (509) (e.g., via one or more adhesives, bonding, welding or the like), and the control element (509) may comprise a slider that is slidably connected to the housing (503). The control element (509) may be advanced toward the contact surface (505) to move the magnet (507) toward the contact surface (505), and may be withdrawn away from the contact surface (505) to move the magnet (507) away from the contact surface (505). It should be appreciated that while shown in FIGS. 5A and 5B as comprising a slider, the control element (509) may be any element or combination of elements capable of moving the magnet (507) relative to the contact surface (505), such as, for example, one or more knobs, triggers, cranks, levers, or the like. For instance, in one variation the control element may have a stapler-like configuration or a squeeze grip having two members connected by a pivot joint. When an operator compresses the stapler-like configuration or squeeze grip by pressing the members toward each other, the magnet may be moved closer to the contact surface. It should also be appreciated that in some embodiments, the magnet may be fixed relative to the contact surface of the magnetic control device.

In some variations, the magnetic control device (501) may comprise a spring (521) configured to bias the control element (509) away from the contact surface (505). In these variations, a user may apply a force to the control element (509) to overcome the bias provided by the spring (521) and advance the control element (509) and magnet (507) toward the contact surface (505). When the force is released, the spring (521) may return the control element (509) and magnet (507) to their original positions. Additionally or alternatively, the magnetic control device (501) may comprise one or more mechanisms configured to temporarily maintain a position of the control element (509). For example, in some variations the housing may comprise a series of teeth (not shown) which may be configured to allow one-way movement of the control element (509) relative to the teeth. In this variation, the teeth may engage the control element (509) and/or the magnet (507) such that the control element (509) may move incrementally toward the contact surface (505), but may be prevented from moving away from the contact surface (505). Each incremental advancement may create an audible sound as the control element (509) and/or magnet (507) advances beyond each individual tooth, which may provide feedback to the user. The teeth may also be moveable to release the engagement between the teeth and the control element (509) and/or magnet (507), which may allow for retraction of the control element (509) and magnet (507) relative to the contact surface (505). In variations where the magnetic control device (501) comprises a spring (521) as shown in FIGS. 5A and 5B, the spring (521) may return the control element (509) and magnet (507) to their original positions when the teeth are disengaged from the control element (509) and/or magnet (507).

The housing and/or control element may have one or more grips or finger rings configured to help allow a user to grab or hold the housing and/or control elements, which may allow for an intuitive and ergonomic user interface, and in some instances may allow the magnetic control device (501) to be manipulated with a single hand. For example, in the embodiment shown in FIGS. 5A and 5B, the housing (503) may comprise two finger rings (513), and the control element (509) may comprise a finger ring (519) such that the finger rings may allow a user to grip the magnetic control device (501) in a syringe-like fashion. For example, a user may place one or more fingers in one or more of the finger rings (513) of the housing (503) and may place a thumb in the finger ring (519) of the control element (509), and may "squeeze" the finger ring (519) of the control element (509) toward the finger rings (513) of the housing (503) to advance the control element (509) (and with it, the magnet (507)) toward the contact surface (505). While the housing (503) is shown in FIGS. 5A and 5B as having two finger rings, it should be appreciated that the housing need not have any finger rings (519), may have one finger ring, or may have three or more finger rings.

In some variations, the magnetic control device may comprise one or more elements configured to releasably secure the magnetic control device to the body. For example, in some variations the magnetic control device may comprise one or more straps (e.g., an elastic strap or the like) which may be connected to the housing, such that the strap may be positioned around a limb (e.g., an arm) of a patient to temporarily connect the magnetic control device to the limb, which may allow the magnetic control device to remain in place without needing to be held by a user.

Systems

Also described here are systems for forming a fistula between two blood vessels. Generally, the systems may comprise a first catheter, which may comprise one or more fistula-forming elements and one or more magnetic elements. The first catheter may comprise any one or more of any of the fistula-forming elements or combination of fistula-forming elements as described in more detail above and in U.S. patent application Ser. No. 13/298,169, which was previously incorporated by reference in its entirety. The first catheter may comprise one or more magnetic elements, which may be any of the magnetic elements described in more detail above. In some variations, the magnetic element may be a permanent magnet or electromagnet generating a locally concentrated magnetic flux, or it may be a ferromagnetic material which may be temporarily magnetized in the presence of a magnetic field. The first catheter may comprise any suitable catheter body and may comprise one or more other elements, such as one or more shape-changing elements or balloons such as described in more detail in U.S. patent application Ser. No. 13/298,169, which was previously incorporated by reference in its entirety.

The systems described here may also comprise a second catheter. In some variations, the second catheter may comprise a fistula-forming element and one or more magnetic elements, but need not. In variations where the second catheter does comprise a fistula-forming element, the second catheter may comprise any one or more of any of the fistula-forming elements or combination of fistula-forming elements as described in more detail above and in U.S. patent application Ser. No. 13/298,169, which was previously incorporated by reference in its entirety. The fistula-forming element of the second catheter may be the same as or different from the fistula-forming element of the first catheter. The second catheter may comprise one or more magnetic elements, which may be any of the magnetic elements described in more detail above. In some variations, the magnetic element may be a permanent magnet or electromagnet generating a locally concentrated magnetic flux, or it may be a ferromagnetic material that may be temporarily magnetized in the presence of a magnetic field. The first catheter may comprise any suitable catheter body and may comprise one or more other elements, such as one or more shape-changing elements or balloons such as described in more detail in U.S. patent application Ser. No. 13/298, 169, which was previously incorporated by reference in its entirety.

The systems described here may further comprise a magnetic control device, such as described in more detail above which can be used to control one or more magnetic elements of the first and/or second catheters from a position external to the body. The magnetic control device may comprise any elements or combinations of elements as described in more detail above.

Methods

Also described here are methods for creating a fistula between two blood vessels. The two blood vessels may be two closely-associated blood vessels, such as a vein and an artery, two veins, etc. Generally, in these methods one or more fistula-forming elements may be activated to bore through, perforate, or otherwise create a passageway between the two blood vessels such that blood may flow directly between the two adjoining blood vessels. When such a fistula is formed, hemostasis may be created without the need for a separate device or structure (e.g., a suture, stent, shunt, or the like) connecting or joining the blood vessels.

Generally, the methods described here comprise accessing a first blood vessel with a first catheter, and advancing the first catheter to a target location within a blood vessel. A second blood vessel may be accessed with a second catheter, and the second catheter may be advanced to a target location within the second vessel. In some of these methods, a first catheter may be advanced into an artery, and a second catheter is advanced into a vein. In other methods, a first catheter may advanced into a first vein and a second catheter is advanced into a second vein. In yet other methods, a first catheter may be advanced into a first artery and a second catheter is advanced into a second artery. The catheters may be advanced in any suitable manner, as described in more detail in U.S. patent application Ser. No. 13/298,169, which was previously incorporated by reference in its entirety, and any of the catheters described in that application may be used.

Once the first and/or second catheters have been advanced into the respective blood vessels, the catheters may be adjusted to affect the positioning of the catheters within the blood vessels and/or the positioning of the blood vessels relative to each other. In variations where a first catheter has been advanced into a first blood vessel and a second catheter has been advanced into a second blood vessel, the first and second catheters may be adjusted to bring at least a portion of the first and second catheters toward each other, which may act to bring the blood vessels in closer approximation. Adjusting the catheters may comprise using one or more magnetic alignment elements, shape-changing members, markers, or balloons or expandable members, as described in more detail in U.S. patent application Ser. No. 13/298,169, which was previously incorporated by reference in its entirety.

Figure 11A:
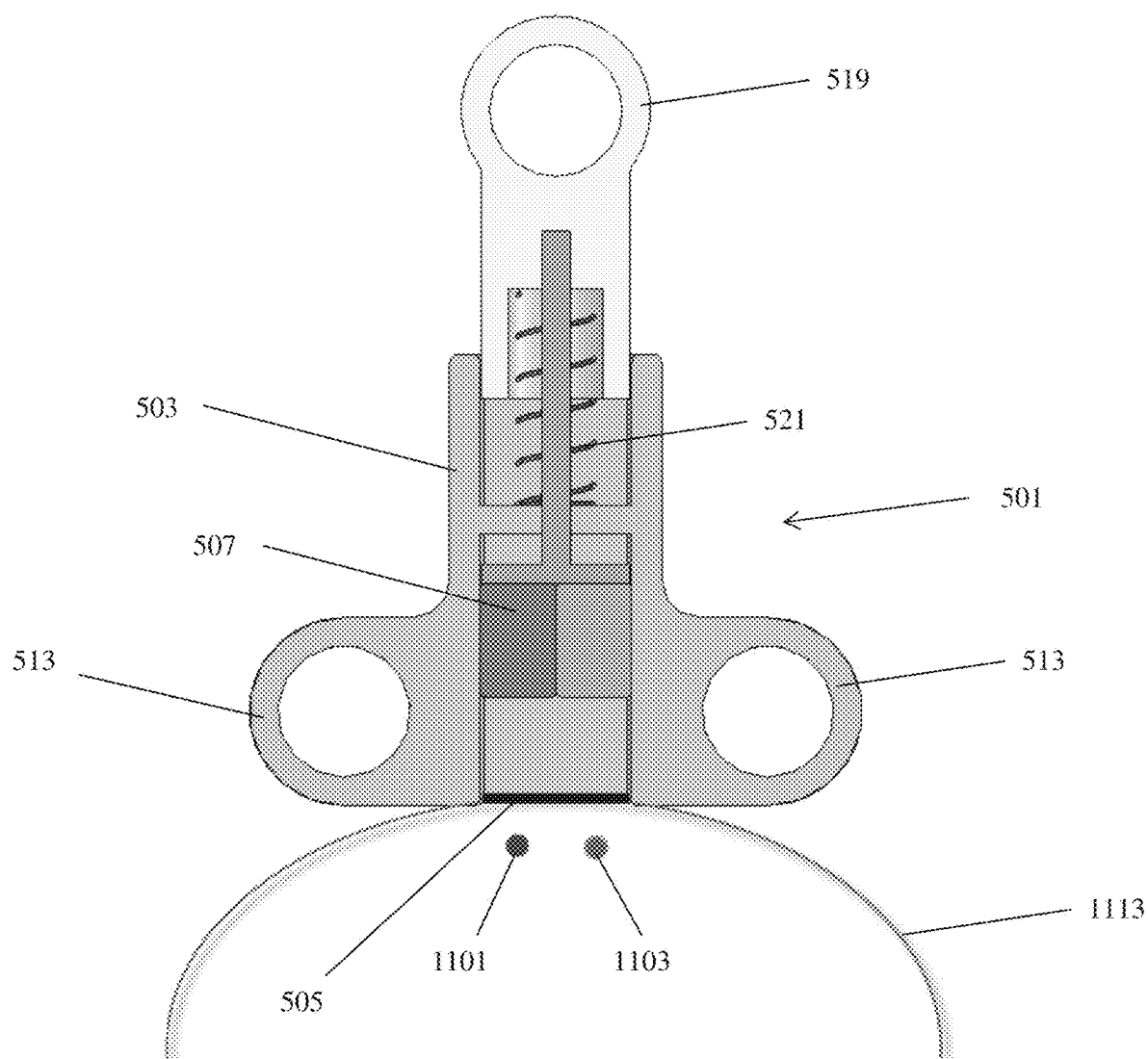
FIGS. 11A-11C are illustrative depictions of a method of manipulating one or more catheters using one or more externally placed magnets.
Figure 11B:
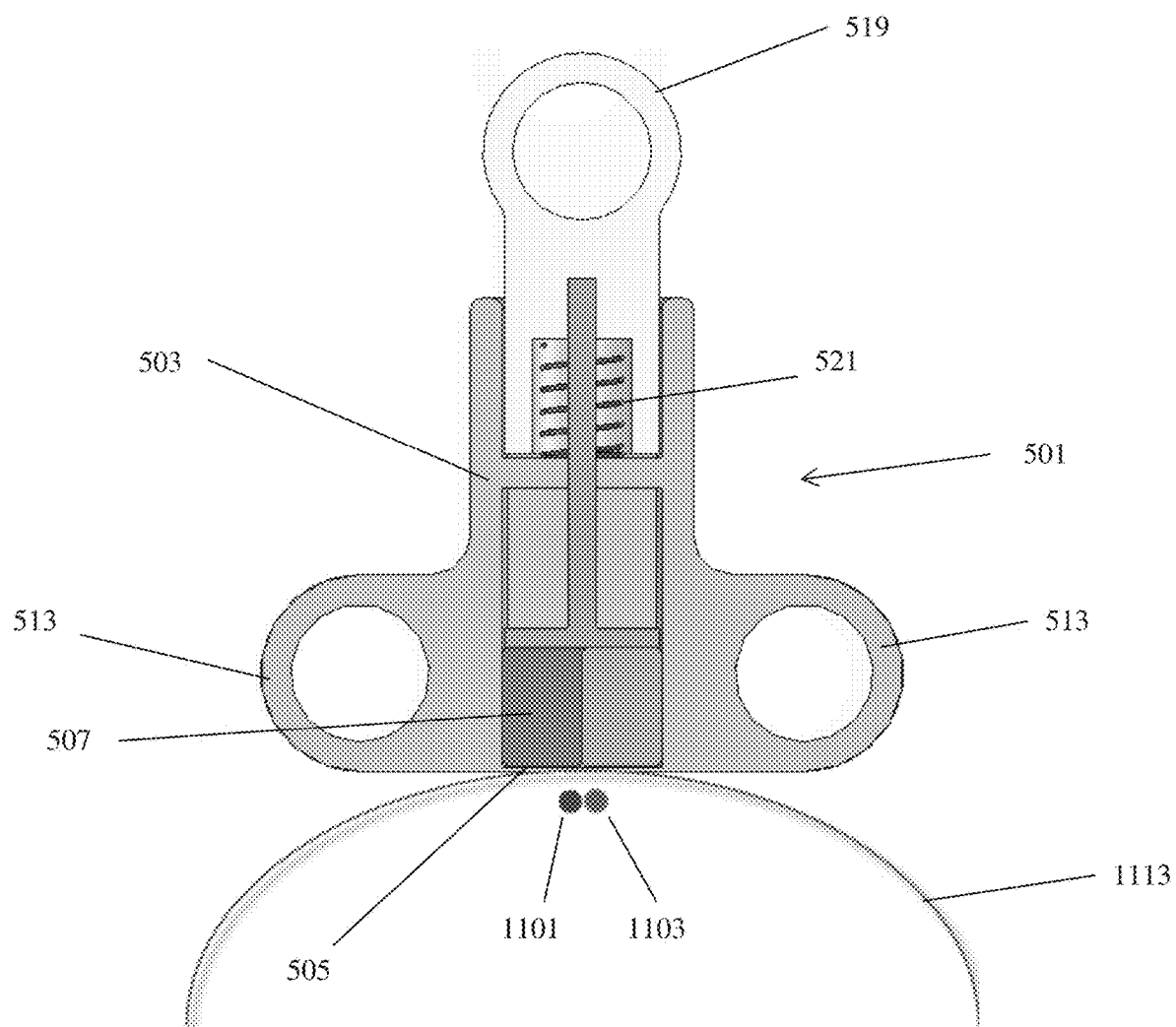
Figure 11C:
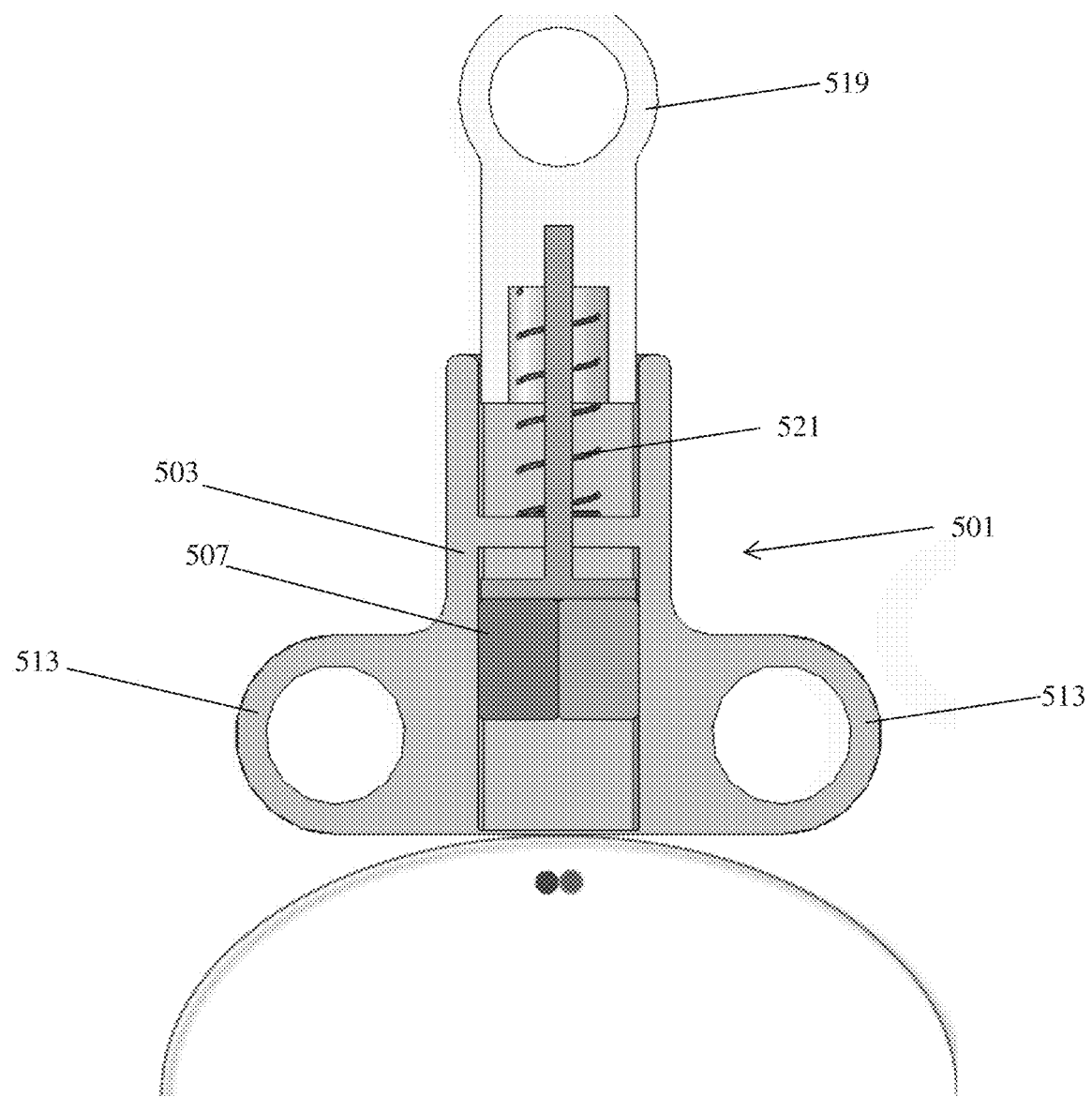

In variations where the first and second catheters comprise one or more magnetic elements, the magnetic elements may result in an attractive force between the first and second catheters, which may pull the catheters toward each other. For example, the first and/or second catheters may comprise one or more magnetic elements having a magnetization pattern such as described in more detail above. Additionally or alternatively, a magnet may be positioned externally to the body and may act to bring the first catheter closer to the second catheter. For example, FIGS. 11A-11C depict a method by which the magnetic control device (501) described above with respect to FIGS. 5A and 5B may be used to bring a first catheter towards a second catheter. For example, a first catheter (1101) may be placed in a first blood vessel (not shown) and a second catheter (1103) may be placed in a second blood vessel (not shown), such as shown in FIG. 11A. The magnetic control device (501) may be positioned to place the contact surface (505) against the skin surface (1113) of a patient near the first and second catheters, such as shown in FIG. 11A. In variations in which the magnetic control device (501) comprises a securing element, the securing element may be used to secure the magnetic control device (501) to the patient.

The magnet (507) may be configured to generate a magnetic field configured to move the first catheter (1101) toward the second catheter (1103) laterally, relative to the magnet, such as described in more detail above. Specifically, the magnet (507) may be advanced (e.g., using a control element (509) as discussed above) toward the contact surface (505) from a retracted position (as shown in FIG. 11A) to an extended position (as shown in FIG. 11B). As the magnet (507) approaches the extended position, the distance between the magnet (507) and the first and second catheters may decrease. This in turn may increase the magnitude of the force that the magnet (507) applies to the first and second catheters. As the force applied to the first and second catheters is increased, the first and second catheters may be urged together, as shown in FIG. 11B.

Once the first and second catheters (1101) and (1103) have moved into closer proximity, the magnet (507) can be moved away from contact surface (505) (e.g., by retracting a control element (509), allowing the spring-bias provided by spring (521) to retract the control element (509), etc.) to move the magnet (507) away from the catheters (1101) and (1103), such as shown in FIG. 11C. When the magnet (507) applies an attractive force to the first and/or second catheters, movement of the magnet (507) away from the skin surface (1113) may pull the first and/or second catheters toward skin surface (1113). In these instances, the contact surface (505) may act as a stop to push against the skin surface (1113) and limit tissue movement towards housing (503) as the magnet (507) is retracted (which may in turn reduce the likelihood that the first and/or second catheters may damage tissue by being pulled toward the skin surface (1113). With the magnet (507) withdrawn, the magnetic control device (501) may be removed from its position relative to the skin surface (1113). The magnetic control device (501) may be removed before, during, or after fistula formation.

Once the catheter or catheters have been positioned and adjusted, one or more fistula-forming elements may be used to create a fistula between the two blood vessels. For example, in some variations, one of the first and second catheters comprises a fistula-forming element (e.g., an electrode, a cutting blade, or the like), while the other catheter does not comprise a fistula-forming element. In other variations, both catheters comprise a fistula-forming element. In some of these variations, the fistula-forming elements of the first and second catheters act to form different fistulas. In other variations, the fistula-forming elements of the first and second catheters interact to form the same fistula. For example, in some variations the first and second catheters each comprise at least one electrode. Any of the methods for using fistula-forming elements to create one or more fistulas described in U.S. patent application Ser. No. 13/298,169, which was previously incorporated by reference in its entirety, may be used. Additionally, one or more balloons may be used to modify a fistula after the fistula has been formed, to affect the blood flow relative to the fistula, or to determine that the fistula has been properly formed, as described in more detail in U.S. patent application Ser. No. 13/298,169, which was previously incorporated by reference in its entirety.

We claim:

1. A system for creating a fistula between two vessels, comprising:
a first catheter comprising a first magnetic element configured to be received within a first vessel;
a second catheter comprising a second magnetic element configured to be received in a second vessel; and
a device for applying a magnetic field to the first and second magnetic elements, wherein:
the magnetic field is configured to move the first catheter laterally toward the second catheter,
at least one of the first and second catheters comprises a fistula-forming element,
the first magnetic element is configured to produce a magnetic field that is stronger on a first side of the first magnetic element than on a second side of the first magnetic element, and
the first magnetic element comprises a plurality of regions each having a polarity, and wherein the plurality of regions of the first magnetic element is configured such that the polarity of each region is rotated a first angle relative to the polarity of an immediately-preceding region in a proximal-to-distal direction of the first magnetic element.

2. The system of claim 1 wherein the fistula-forming element is an electrode.

3. The system of claim 1 wherein the second magnetic element comprises a plurality of regions each having a polarity, and wherein the plurality of regions of the second magnetic element is configured such that the polarity of each region is rotated a second angle relative to the polarity of an immediately-preceding region proximal-to-distal direction.

4. The system of claim 3 wherein the first angle is the same as the second angle.

5. The system of claim 3 wherein the first angle is about 90 degrees.

6. The system of claim 3 wherein the first angle is about 45 degrees.

7. The system of claim 3 wherein the first angle is about 30 degrees.

8. The system of claim 3 wherein the plurality of regions of the first magnetic element is configured such that the polarity of each region is rotated a first angle clockwise relative to the polarity of an immediately-preceding region in a proximal-to-distal direction, and wherein the plurality of regions of the second magnetic element is configured such that the polarity of each region is rotated a second angle counter-clockwise relative to the polarity of an immediately-preceding region proximal to-distal direction.

9. A system for forming a fistula between two vessels, comprising:
- a first catheter comprising a first magnetic element;
- a second catheter comprising a second magnetic element, wherein at least one of the first and second catheters comprises a fistula-forming element; and
- a device for applying a magnetic field to the first and second magnetic elements, comprising a magnet inside a housing, wherein the magnet is moveable within the housing, and wherein the magnet is configured to generate a magnetic field that, when applied simultaneously to the first and second magnetic elements, is capable of increasing an attractive force between the first and second magnetic elements; and
- wherein the magnetic field is configured to move the first catheter laterally toward the second catheter.

10. The system of claim 9, wherein the fistula-forming element comprises an electrode.

11. The system of claim 9, wherein the first magnetic element comprises a plurality of regions each having a polarity, and wherein the plurality of regions of the first magnetic element is configured such that the polarity of each region is rotated a first angle relative to the polarity of an immediately-preceding region in a proximal-to-distal direction.

12. The system of claim 11, wherein the second magnetic element comprises a plurality of regions each having a polarity, and wherein the plurality of regions of the second magnetic element is configured such that the polarity of each region is rotated a second angle relative to the polarity of an immediately-preceding region proximal-to distal direction.

13. A method of forming a fistula between a first blood vessel and a second blood vessel of a patient comprising:
- advancing a first catheter into the first blood vessel, wherein the first catheter comprises a first magnetic element;
- advancing a second catheter into the second blood vessel, wherein the second catheter comprises a second magnetic element, and wherein at least one of the first and second catheters comprises a fistula-forming element;
- positioning an external magnet external the patient, wherein the magnet produces a magnetic field;
- increasing an attractive force between the first and second magnetic elements when applying the magnetic field simultaneously to the first and second magnetic elements, wherein the magnetic field is configured to move the first catheter laterally toward the second catheter; and
- forming a fistula with the fistula-forming element.

14. The method of claim 13 wherein the positioning the external magnet external to the body comprises positioning the external magnet using a magnetic control device, wherein the magnetic device comprises the external magnet and a housing having a contact surface.

15. The method of claim 14 further comprising positioning the contact surface of the housing in contact with a skin surface of the patient.

16. The method of claim 14 further comprising moving the external magnet toward the contact surface to increase a force applied by the magnetic field to at least one of the first and second catheters.

17. The method of claim 13 wherein the fistula-forming element is an electrode, and wherein forming the fistula with the fistula-forming element comprises ablating tissue with the electrode.

18. The method of claim 13 wherein the first blood vessel is a vein and the second blood vessel is an artery.

* * * * *